US009061084B2

(12) United States Patent
Ohtsuka et al.

(10) Patent No.: US 9,061,084 B2
(45) Date of Patent: Jun. 23, 2015

(54) FINE PARTICLE DIFFUSION DEVICE

(75) Inventors: Masaki Ohtsuka, Osaka (JP); Hideyuki Karita, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 1105 days.

(21) Appl. No.: 13/059,574

(22) PCT Filed: Apr. 15, 2009

(86) PCT No.: PCT/JP2009/057563
§ 371 (c)(1), (2), (4) Date: Feb. 17, 2011

(87) PCT Pub. No.: WO2010/023989
PCT Pub. Date: Mar. 4, 2010

(65) Prior Publication Data

US 2011/0139889 A1 Jun. 16, 2011

(30) Foreign Application Priority Data

Aug. 26, 2008 (JP) ................................ 2008-217205
Aug. 26, 2008 (JP) ................................ 2008-217236

(51) Int. Cl.
| | |
|---|---|
| *A61L 9/22* | (2006.01) |
| *A61L 9/12* | (2006.01) |
| *A01M 1/20* | (2006.01) |
| *B03C 3/32* | (2006.01) |
| *B03C 3/38* | (2006.01) |
| *F24F 1/00* | (2011.01) |
| *F24F 3/16* | (2006.01) |

(52) U.S. Cl.
CPC .............. *A61L 9/122* (2013.01); *A01M 1/2033* (2013.01); *A61L 9/22* (2013.01); *B03C 3/32* (2013.01); *B03C 3/383* (2013.01); *F24F 2001/0096* (2013.01); *F24F 2003/1635* (2013.01); *F24F 2003/1682* (2013.01)

(58) Field of Classification Search
CPC .................................... A61L 9/04; A61L 9/22
USPC .............. 422/123–124; 361/225, 230; 239/34
See application file for complete search history.

(56) References Cited

U.S. PATENT DOCUMENTS

2006/0263280 A1 11/2006 Ohtsuka et al.
2006/0285269 A1* 12/2006 Ohtsuka et al. ............... 361/225
2010/0001205 A1 1/2010 Sekoguchi et al.

FOREIGN PATENT DOCUMENTS

JP 2004-293893 A 10/2004
JP 2004-363088 A 12/2004

(Continued)

OTHER PUBLICATIONS

Machine translation of JP2005-337611 provided by esp@cenet (retrieved May 28, 2011).*

*Primary Examiner* — Sean E Conley
(74) *Attorney, Agent, or Firm* — Birch, Stewart, Kolasch & Birch, LLP

(57) ABSTRACT

A fine particle diffusion device includes: a first outlet (10*a* to 10*c*) through which a first air current is discharged to a space above a living space within a living room; a second outlet (10*d*) which is arranged below the first outlet (10*a* to 10*c*) and through which a second air current is discharged to a space below the first air current; and a fine particle generation device (17) which generates fine particles. Here, the fine particles generated by the fine particle generation device (17) are discharged into the living room, and the concentration of the fine particles discharged through the first outlet (10*a* to 10*c*) is lower than the concentration of the fine particles discharged through the second outlet (10*d*).

7 Claims, 26 Drawing Sheets

(56) References Cited

FOREIGN PATENT DOCUMENTS

| | | |
|---|---|---|
| JP | 2005-83649 A | 3/2005 |
| JP | 2005-95402 A | 4/2005 |
| JP | 2005-337611 A | 12/2005 |
| JP | 2006-162220 A | 6/2006 |
| JP | 2007-103026 A | 4/2007 |
| JP | 2008-192556 A | 8/2008 |
| RU | 1084000 A1 | 4/1984 |
| WO | WO2006001116 * | 1/2006 |

* cited by examiner

FINE PARTICLE DIFFUSION DEVICE

TECHNICAL FIELD

The present invention relates to a fine particle diffusion device that discharges fine particles and diffuses them into a room. The present invention also relates to a fine particle diffusion device that discharges ions and diffuses them into a room.

BACKGROUND ART

A conventional fine particle diffusion device is disclosed in patent document 1. In the conventional fine particle diffusion device, a blower fan is provided within an enclosure in which an outlet is opened in its front surface, and the blower fan and the outlet are coupled to each other by an air blow path. A fine particle generation device for generating ions that are fine particles is arranged within the air blow path.

An air current generated by the blower fan flows in the air flow path, and the air current containing the fine particles generated by the fine particle generation device is discharged through the outlet. The air flow path is formed to extend in the lateral direction, and the air current discharged through the outlet extends in the lateral direction, with the result that the fine particles are diffused into a living room. In this way, positive ions and negative ions are supplied to the living room, and thus it is possible to kill airborne bacteria within the living room.

Figure 20:
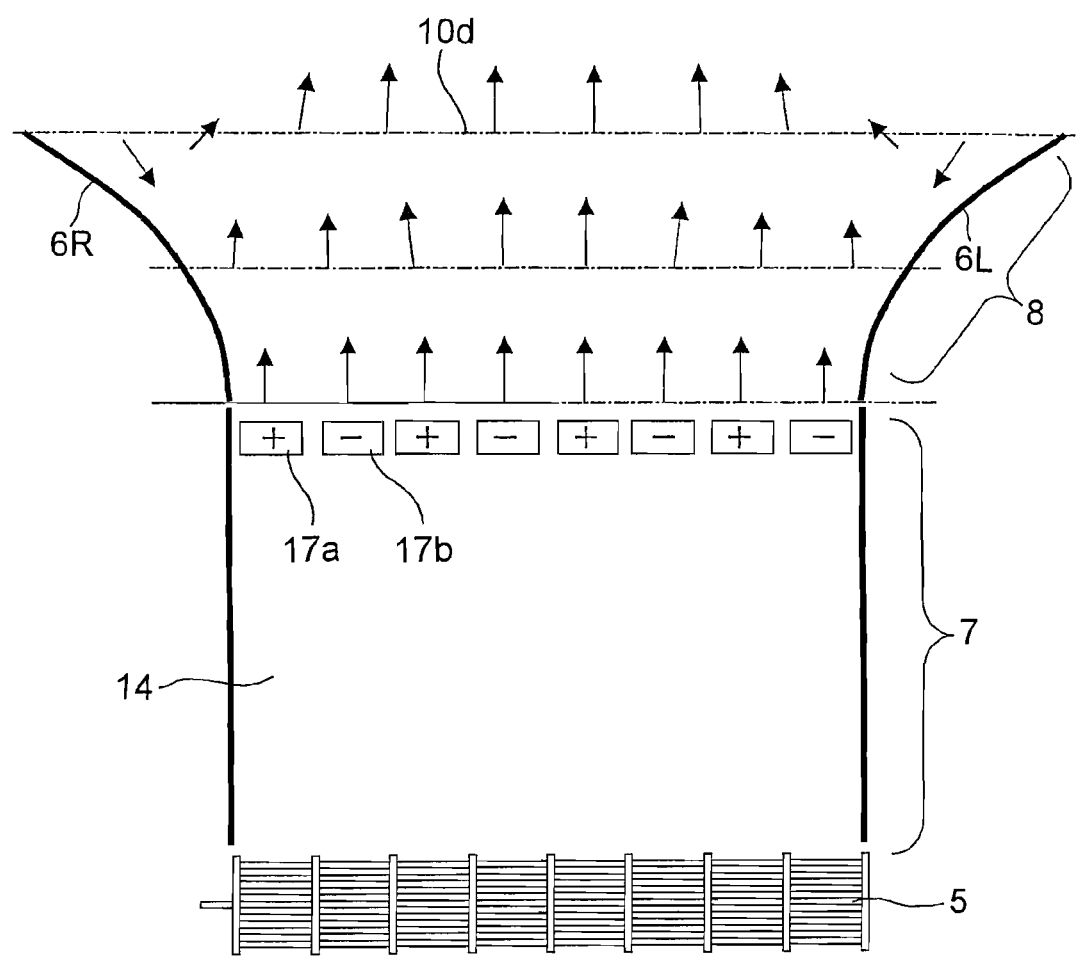

Patent document 1 also discloses a configuration in which an air flow path that is divided into upper and lower portions is included (see FIG. 20). In this configuration, fine particles are discharged through an outlet such that they extend in the vertical direction. Thus, the fine particles are diffused into a living room such that they extend from top to bottom within the living room.

RELATED ART DOCUMENT

Patent Document

Patent document 1: Japanese Patent No. 3797993 (Pages 4-18 and FIGS. 1 and 20)

DISCLOSURE OF THE INVENTION

Problems to be Solved by the Invention

However, since the conventional fine particle diffusion device discharges fine particles of substantially the same concentration to a living space and an area above the living space within the living room, a sufficient number of fine particles such as ions may not be supplied to the living space. In particular, in a floor or the like where a living room has a high ceiling, fine particles such as ions are diffused to the upper area where there are no people, and the number of fine particles in the living space is significantly reduced. Hence, a problem is encountered in that it is impossible to sufficiently obtain effective effects such as sterilization and relaxation resulting from the fine particles present within the living space. The same problem is encountered when fine particles, other than ions, of an aromatic substance, a deodorant, an insecticide, a bactericide or the like are generated by the fine particle generation device.

Since the air flow path is formed to extend laterally, an air current bends and flows in the air flow path. Hence, positive ions and negative ions included in the air current are more likely to collide with each other; disadvantageously, the number of ions discharged into the living room is reduced, and thus the sterilization performance is reduced.

An object of the present invention is to provide a fine particle diffusion device that can sufficiently supply fine particles to a living space. Another object of the present invention is to provide a fine particle diffusion device that can sufficiently supply ions to a living space and can enhance a sterilization performance.

Means for Solving the Problem

To achieve the above objects, according to the present invention, there is provided a fine particle diffusion device including: a first outlet through which a first air current is discharged upward; a second outlet which is arranged below the first outlet and through which a second air current is discharged to a space below the first air current; and a fine particle generation device which generates fine particles. In the fine particle diffusion device, the fine particles generated by the fine particle generation device are discharged, and the concentration of the fine particles discharged through the first outlet is lower than the concentration of the fine particles discharged through the second outlet.

In this configuration, the first air current is discharged upward through the first outlet at the upper portion, and the second air current is discharged through the second outlet at the lower portion to the space below the first air current. The fine particles generated by the fine particle generation device are included in the second air current; the fine particles are supplied to a living space or the like within a living room. The first air current includes the fine particles of a concentration lower than the concentration of the second air current, and is discharged to a space above the living room. Thus, the first air current functions as an air curtain, and this reduces the upward diffusion of the fine particles included in the second air current. It is therefore possible to supply most of the fine particles generated by the fine particle generation device to the living space and obtain the effects of sterilization, relaxation and the like. The case where the first air current including no fine particles is discharged is included.

The present invention is characterized in that, in the fine particle diffusion device configured as described above, the fine particles are not discharged through the first outlet. In this configuration, the second outlet is opened to an end surface of a duct where the fine particle generation device is arranged, and the fine particles generated by the fine particle diffusion device are discharged through the second outlet via the duct.

The present invention is characterized in that, in the fine particle diffusion device configured as described above, the speed of the first air current is higher than the speed of the second air current. In this configuration, the slow second air current is discharged to the living space, and the fine particles are supplied to the living space without the wind being sensed by a person. Moreover, the first air current reliably forms the air curtain.

The present invention is characterized in that, in the fine particle diffusion device configured as described above, the second air current is adjacent to the first air current. In this configuration, the fine particles included in the second air current are supplied to the far parts of the living room by being drawn by the first air current at the lower portion.

The present invention is characterized in that, in the fine particle diffusion device configured as described above, the first outlet is divided into an upper portion and a lower portion, and the speed of the first air current discharged through the upper portion of the first outlet is higher than the speed of the first air current discharged through the lower portion. In this configuration, as the first air current faster than the second air current moves upward, its speed is gradually increased. Thus, the disturbance of the air currents is reduced.

The present invention is characterized in that, in the fine particle diffusion device configured as described above, the second air current is discharged through the second outlet such that the second air current extends in a vertical direction. In this configuration, the second outlet extends in a vertical direction, for example, in the form of a horn, and thus the fine particles are diffused vertically.

The present invention is characterized in that, in the fine particle diffusion device configured as described above, the second air current is discharged through the second outlet such that the second air current extends in a lateral direction. In this configuration, the second outlet extends in a lateral direction, for example, in the form of a horn, and thus the fine particles are diffused laterally.

The present invention is characterized in that, in the fine particle diffusion device configured as described above, the first air current is discharged through the first outlet such that the first air current extends in a lateral direction. In this configuration, the first outlet extends in a lateral direction, for example, in the form of a horn, and the air curtain is reliably formed by the first air current.

The present invention is characterized in that, in the fine particle diffusion device configured as described above, the lateral width of the first outlet is sufficiently greater than the height of the first outlet. In this configuration, the air curtain is reliably formed by the first air current.

The present invention is characterized in that, in a fine particle diffusion device that includes a fine particle generation device for generating fine particles and that discharges the fine particles through an outlet by driving of a blower fan, an air flow path coupling the blower fan to the outlet includes a plurality of vertical division passages that divide the outlet vertically, and the speed of an air current flowing in one of the vertical division passages at an upper portion is higher than the speed of an air current flowing in one of the vertical division passages at a lower portion.

In this configuration, when the blower fan is driven, the air currents flow in the vertical division passages, are smoothed, contain the fine particles generated by the fine particle generation device and are discharged through the outlet. Here, the air current at the upper portion of the outlet functions as the air curtain, and the fine particles included in the air current at the lower portion are supplied to the lower portion of the living room.

The present invention is characterized in that, in the fine particle diffusion device configured as described above, the fine particle generation device is arranged in the vertical division passage at the lower portion. In this configuration, the fine particles are included in the slow air current discharged through the lower portion of the outlet, and are supplied to the living space without the wind being sensed by a person.

The present invention is characterized in that, in the fine particle diffusion device configured as described above, the air flow path extends upward from the blower fan and bends frontward, and the air flow path extends from the vicinity of the blower fan to the outlet to form the vertical division passages.

In this configuration, the air current flowing in the air flow path flows upward, bends frontward and is discharged through the outlet. When the air current flowing upward in the air flow path bends frontward, it moves upward due to the inertia thereof, and thus the air current is more likely to move apart from the lower wall and along the upper wall. Therefore, the speed of the air current flowing in the upper portion of the air flow path is higher than that of an air current flowing in the lower portion. Here, when a large amount of the air current moves apart from the lower wall, an air current flowing in the opposite direction is generated on the side of the lower wall, and thus the air current is disturbed. The vertical division passages are provided to extend from the vicinity of the blower fan; the wetted perimeter (a perimeter surrounding a cross section) of the cross section of a flow path is increased due to the vertical division passages. Hence, the air currents are affected more by the viscosity than by the inertia, and thus the air currents are more likely to move along the wall surfaces of the vertical division passages. Thus, the separation of the air currents is reduced and the air currents are prevented from being disturbed The present invention is characterized in that, in the fine particle diffusion device configured as described above, the air flow path is provided with an upper wall having a curved surface portion and a lower wall having a curved surface portion, extends upward from the blower fan and bends frontward and extends to the outlet from the upstream side of a position intersecting the center of the curved surface portion of the upper wall and the center of the curved surface portion of the lower wall to form the vertical division passages.

In this configuration, the air current flowing in the air flow path flows upward, bends frontward in the curved surface portion and is discharged through the outlet. When the air current flowing upward in the air flow path bends frontward, it moves upward due to the inertia thereof, and thus the air current is more likely to move apart from the lower wall and along the upper wall. Therefore, the speed of the air current flowing in the upper portion of the air flow path is higher than that of the air current flowing in the lower portion. Here, when a large amount of the air current moves apart from the lower wall, an air current flowing in the opposite direction is generated on the side of the lower wall, and thus the air current is disturbed. The vertical division passages are provided on the upstream side of the position intersecting the center of the curved surface portion of the upper wall and the center of the curved surface portion of the lower wall; the wetted perimeter of the cross section of the vertical division passages is increased. Hence, the air currents are more likely to move along the wall surfaces of the vertical division passages. Thus, the separation of the air currents is reduced and the air currents are prevented from being disturbed The present invention is characterized in that, in the fine particle diffusion device configured as described above, the blower fan is formed with a cross flow fan, and the vertical division passage at the lower portion is arranged on the inner circumferential side of the blower fan as compared with the vertical division passage at the upper portion. In this configuration, the air current discharged from the inner circumferential side of an air outlet port of the blower fan formed with a cross flow fan is guided to the vertical division passage at the lower portion, and the air current discharged from the outer circumferential side is guided to the vertical division passage at the upper portion. The inner circumferential side of the air outlet port indicates the front of the rotational direction of the rotor; the outer circumferential side indicates the back of the rotational direction of the rotor. In this way, the speed of the air current flowing in the vertical division passage at the upper portion is increased due to the centrifugal force.

The present invention is characterized in that, in the fine particle diffusion device configured as described above, the vertical division passages have a vertically increasing width portion that increases the width thereof as the vertically increasing width portion extends from the upstream side to the downstream side and that extends an air current in a vertical direction, and the cross section of the vertically increasing width portion perpendicular to the air current is formed in the shape of a laterally extending slit.

In this configuration, the air current flowing in the vertical division portion is gradually extended in the vertical direction by the vertically increasing width portion, and is discharged through the outlet such that it extends vertically. The cross section of the vertically increasing width portion is formed in the shape of a laterally extending slit, and the upper and lower walls are long in the lateral direction. Hence, the areas of portions of the upper and lower wall surfaces of the vertical division passages in contact with the air currents flowing in the air flow path are increased. It is therefore possible to extend the air currents in the vertical direction without the air currents separating from the wall surfaces such that the air currents easily flow along the upper and lower walls of the vertical division passages.

The present invention is characterized in that, in the fine particle diffusion device configured as described above, the vertical division passages have, on the downstream side of the vertically increasing width portion, a laterally increasing width portion that increases the width thereof as the laterally increasing width portion extends from the upstream side to the downstream side and that extends an air current in a lateral direction. In this configuration, the air current flowing in the vertical division portion is extended in the vertical direction by the vertically increasing width portion and is extended in the lateral direction by the laterally increasing width portion, and is discharged through the outlet such that the air current extends vertically and laterally.

The present invention is characterized in that, in the fine particle diffusion device configured as described above, one of the vertical division passages having the fine particle generation device arranged therein is provided with a narrowed portion that narrows a flow path either at a position where the fine particle generation device is arranged or on the upstream side thereof. In this configuration, the air current is narrowed and smoothed either on the fine particle generation device or on the upstream side, and, since the speed of the air current is increased, the concentration of the fine particles near the fine particle generation device is decreased. The air current path including the fine particles is extended by the vertically increasing width portion.

The present invention is characterized in that, in the fine particle diffusion device configured as described above, the laterally increasing width portion has a plurality of thin passages that laterally divide each of the vertical division passages, and the lateral width of each of the thin passages is increased as the thin passage extends from the upstream side to the downstream side. In this configuration, the areas of portions of the left and right wall surfaces of the thin passages in contact with the air currents flowing in the air flow path through the thin passages that laterally divide the vertical division passages are increased. It is therefore possible to extend the air currents in the lateral direction without the air currents separating from the wall surfaces such that the air currents flow along the left and right walls of the thin passages.

The present invention is characterized in that, in the fine particle diffusion device configured as described above, the fine particles generated by the fine particle generation device include any one of an ion, an aromatic substance, a deodorant, an insecticide and a bactericide.

The present invention is characterized in that a fine particle diffusion device includes: an ion generation device including a first ion generation portion that generates one of a positive ion and a negative ion and a second ion generation portion that generates the other of the positive ion and the negative ion; a blower fan; and an air flow path that guides, by driving of the blower fan, the ions generated by the ion generation device to an outlet. In the fine particle diffusion device, the air flow path includes a plurality of lateral division passages whose lateral widths are increased as the lateral division passages extend from the upstream side to the downstream side and which are divided laterally, and one of the positive ion and the negative ion flows in each of the lateral division passages.

In this configuration, the air current flowing in the air flow path is discharged through the outlet by the driving of the blower fan into the living room. The air flow path is divided in the lateral direction by the lateral division passages; for example, the positive ion generated by the first ion generation portion flows in one of the lateral division passages, and the negative ion generated by the second ion generation portion flows in another of the lateral division passages.

The present invention is characterized in that, in the fine particle diffusion device configured as described above, one of the first and second ion generation portions is arranged either in each of the lateral division passages or in the vicinity of an open end of each of the lateral division passages on the air inflow side.

In this configuration, for example, the first ion generation portion is arranged in one of the lateral division passages and the positive ion flows therein, and the second ion generation portion is arranged in another of the lateral division passages and the negative ion flows therein. The first ion generation portion is arranged in the vicinity of the open end of one of the lateral division passages on the air inflow side and the positive ion flows in the lateral division passage; the second ion generation portion is arranged in the vicinity of the open end of another of the lateral division passages on the air inflow side and the negative ion flows in the lateral division passage.

The present invention is characterized in that, in the fine particle diffusion device configured as described above, polarities of the ions generated by the first and second ion generation portions are switched every predetermined period. In this configuration, for example, the positive ion generated by the first ion generation portion flows in one of the lateral division passages, and the negative ion generated by the second ion generation portion flows in another of the lateral division passages. When the predetermined period elapses, the negative ion generated by the first ion generation portion flows in one of the lateral division passages, and the positive ion generated by the second ion generation portion flows in another of the lateral division passages.

The present invention is characterized in that, in the fine particle diffusion device configured as described above, the positive ion flows in one of the lateral division passages adjacent to each other and the negative ion flows in the other of the adjacent lateral division passages. In this configuration, the positive ion and the negative ion are discharged from the two adjacent lateral division passages.

The present invention is characterized in that, in the fine particle diffusion device configured as described above, the first and second ion generation portions are arranged either in each of the lateral division passages or in the vicinity of an open end of each of the lateral division passages on an air inflow side, and the first and second ion generation portions are alternately driven.

In this configuration, the positive ion generated by the first ion generation portion flows in one of the lateral division passages, and the negative ion generated by the second ion generation portion flows in another of the lateral division passages. When the predetermined period elapses, the negative ion generated by the second ion generation portion flows in one of the lateral division passages, and the positive ion generated by the first ion generation portion flows in another of the lateral division passages.

The present invention is characterized in that, in the fine particle diffusion device configured as described above, the air flow path is provided with a left wall having a curved surface portion and a right wall having a curved surface portion and extends toward both sides, and open ends of the lateral division passages on the air inflow side are formed on the upstream side of a position intersecting the center of the curved surface portion of the left wall and the center of the curved surface portion of the right wall.

In this configuration, the air current flowing in the air flow passage is more likely to flow straight due to the inertia thereof, and moves apart from the curved surface portions of the left and right walls, with the result that the air current is easily disturbed. The lateral division passages are provided to extend toward the outlet from the upstream side of the position intersecting the center of the curved surface portion of the left wall and the center of the curved surface portion of the right wall. The wetted perimeter (a perimeter surrounding a cross section) of the cross section of the flow path is increased due to the lateral division passages, and thus the areas of portions of the left and right wall surfaces in contact with the air current are increased. Hence, the air current curving and flowing easily flows along the left and right wall surfaces of the lateral division passage, and the separation from the wall surfaces is reduced. It is therefore possible to reduce the disturbance of the air current and laterally extend the air current flowing in the air flow path.

Figure 13:
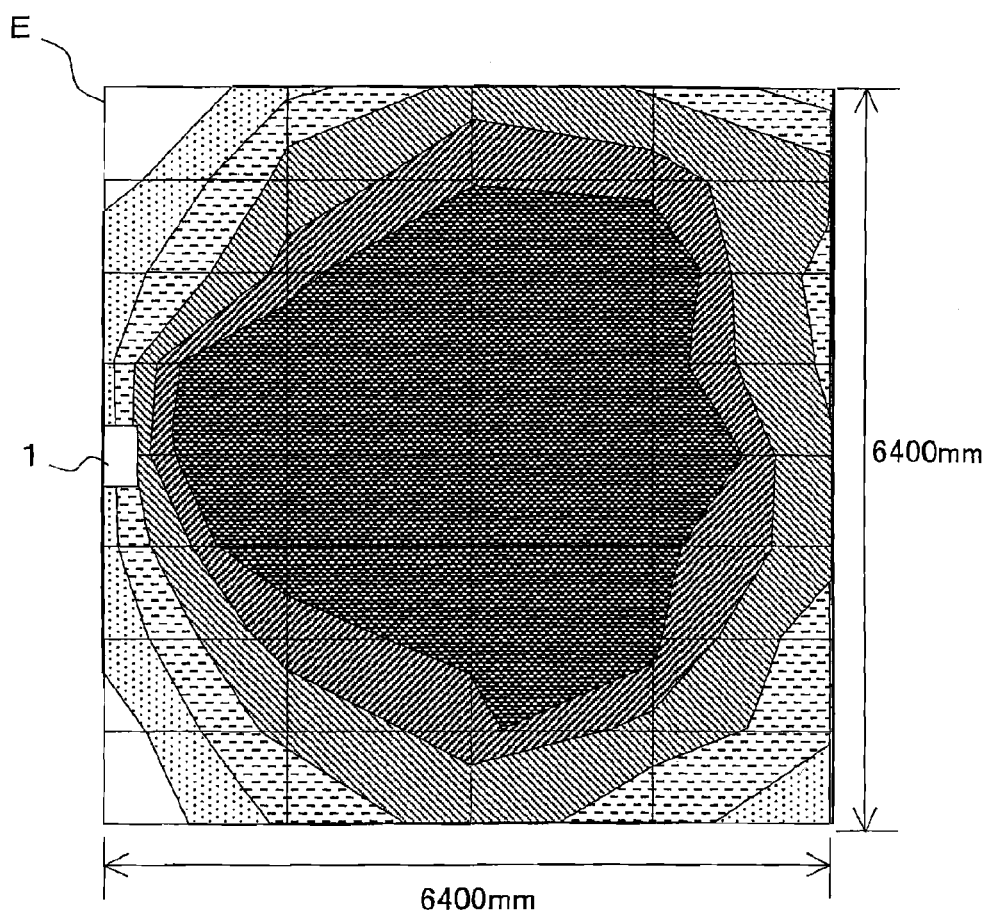
Figure 14:
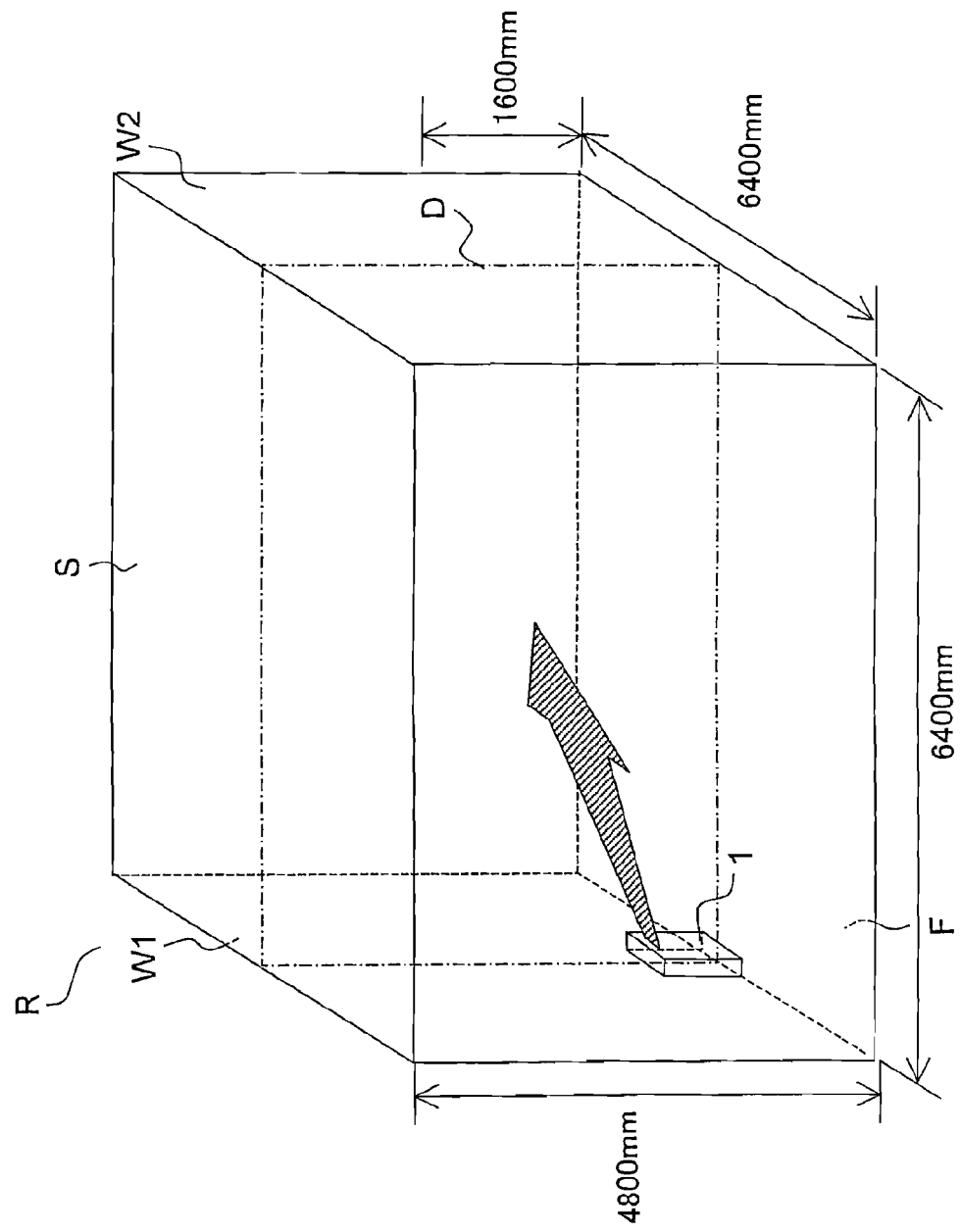
Figure 15:
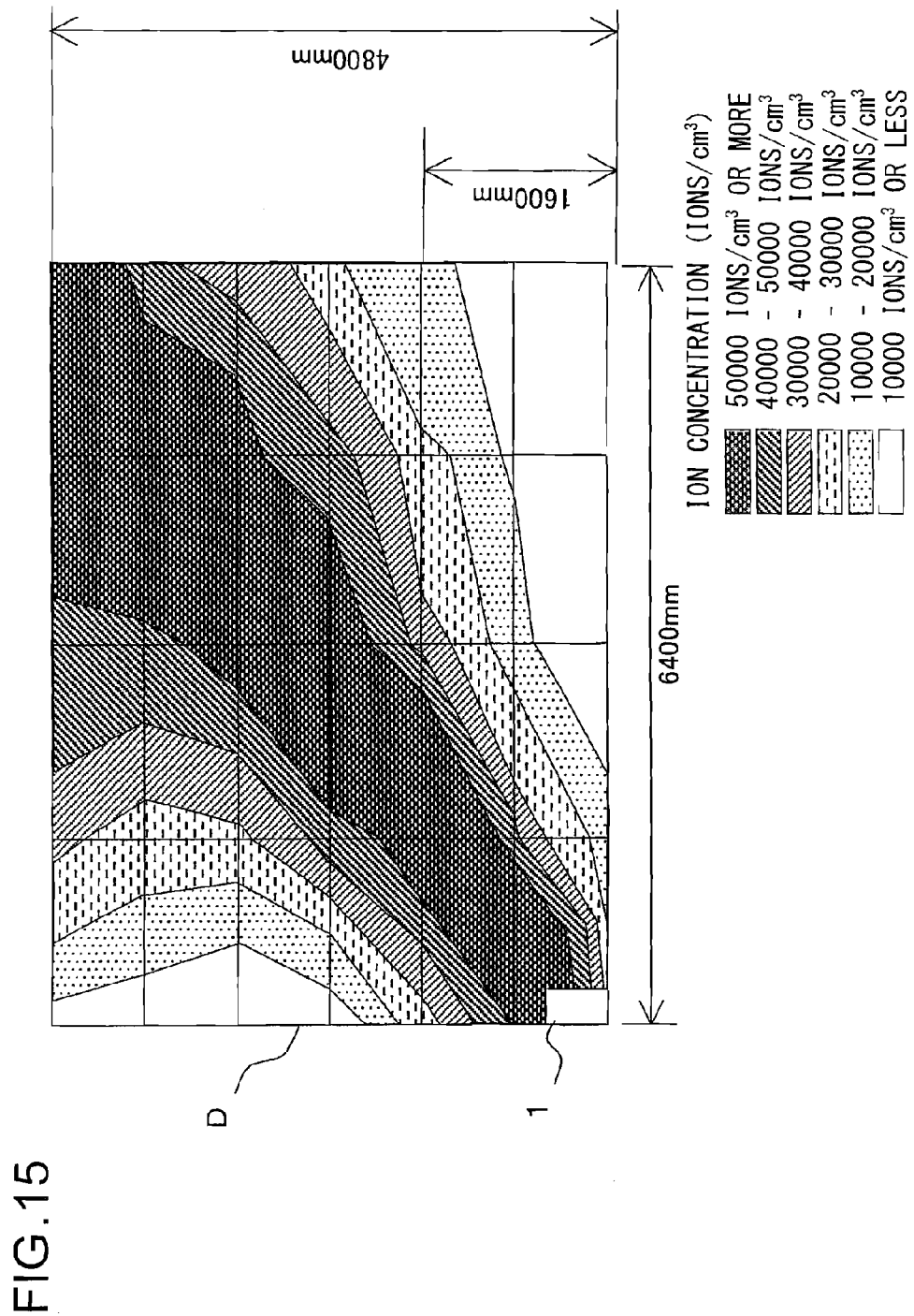
Figure 16:
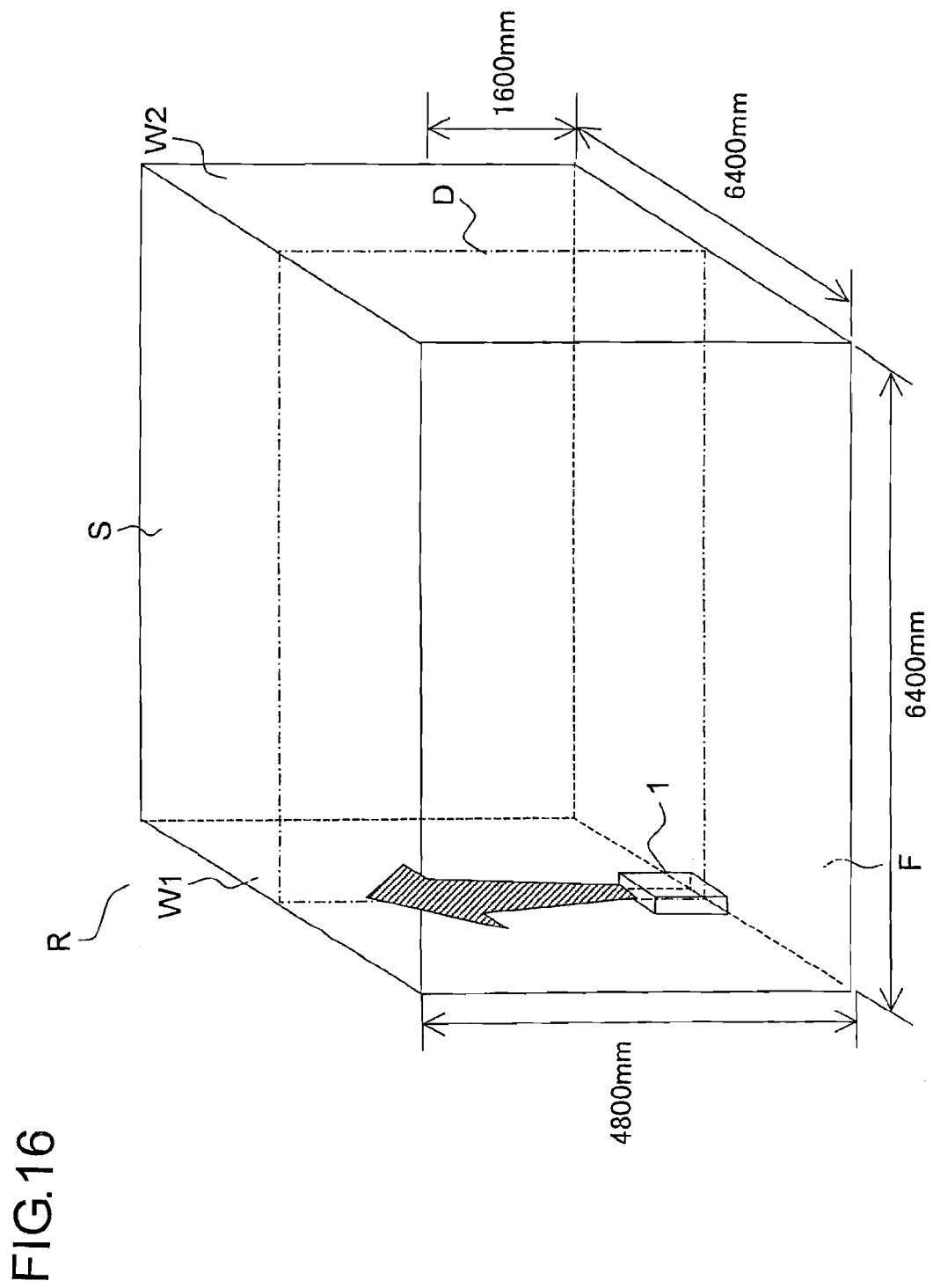
Figure 17:
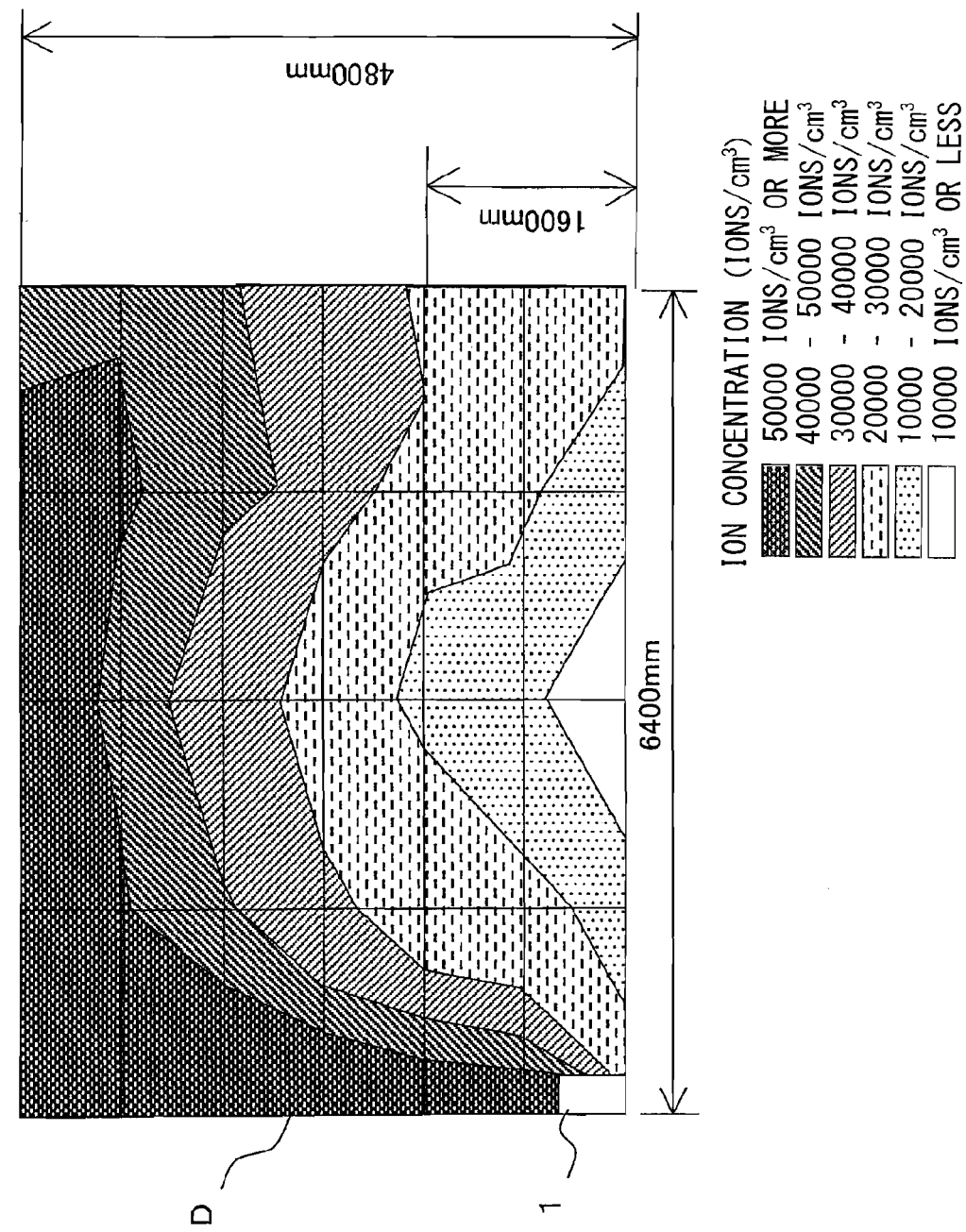
Figure 18:
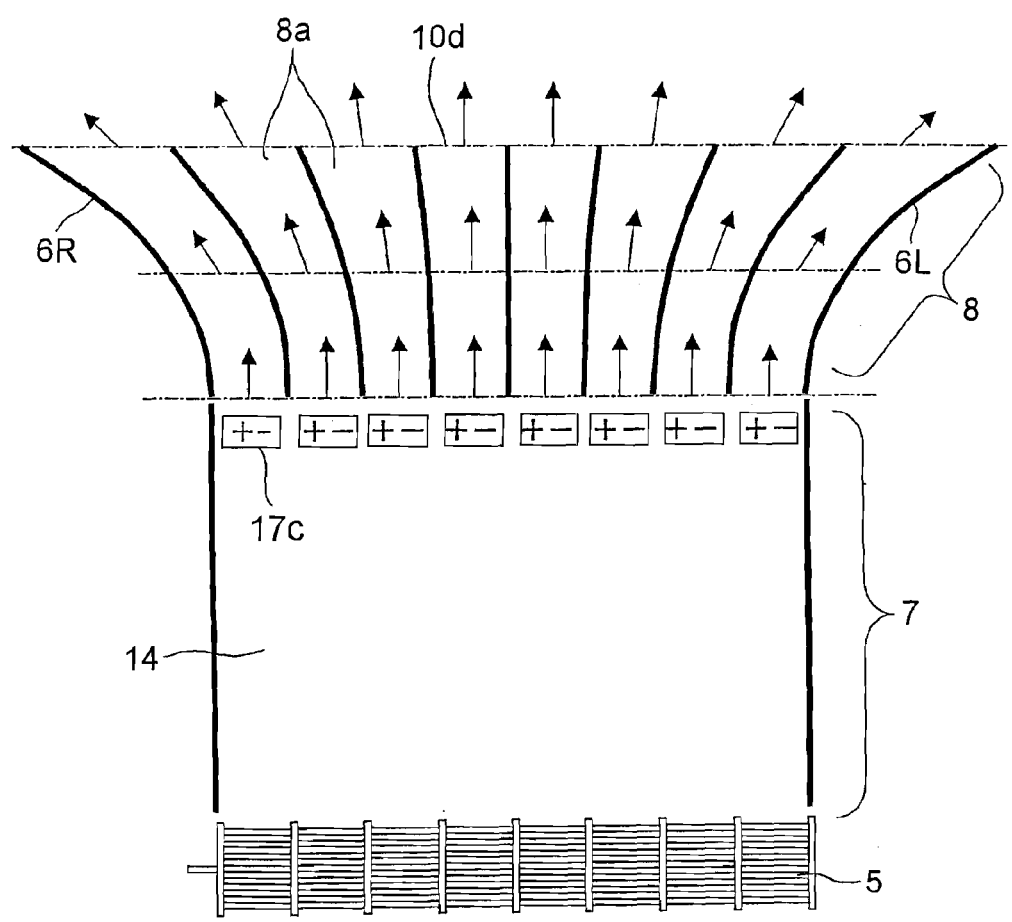
Figure 19:
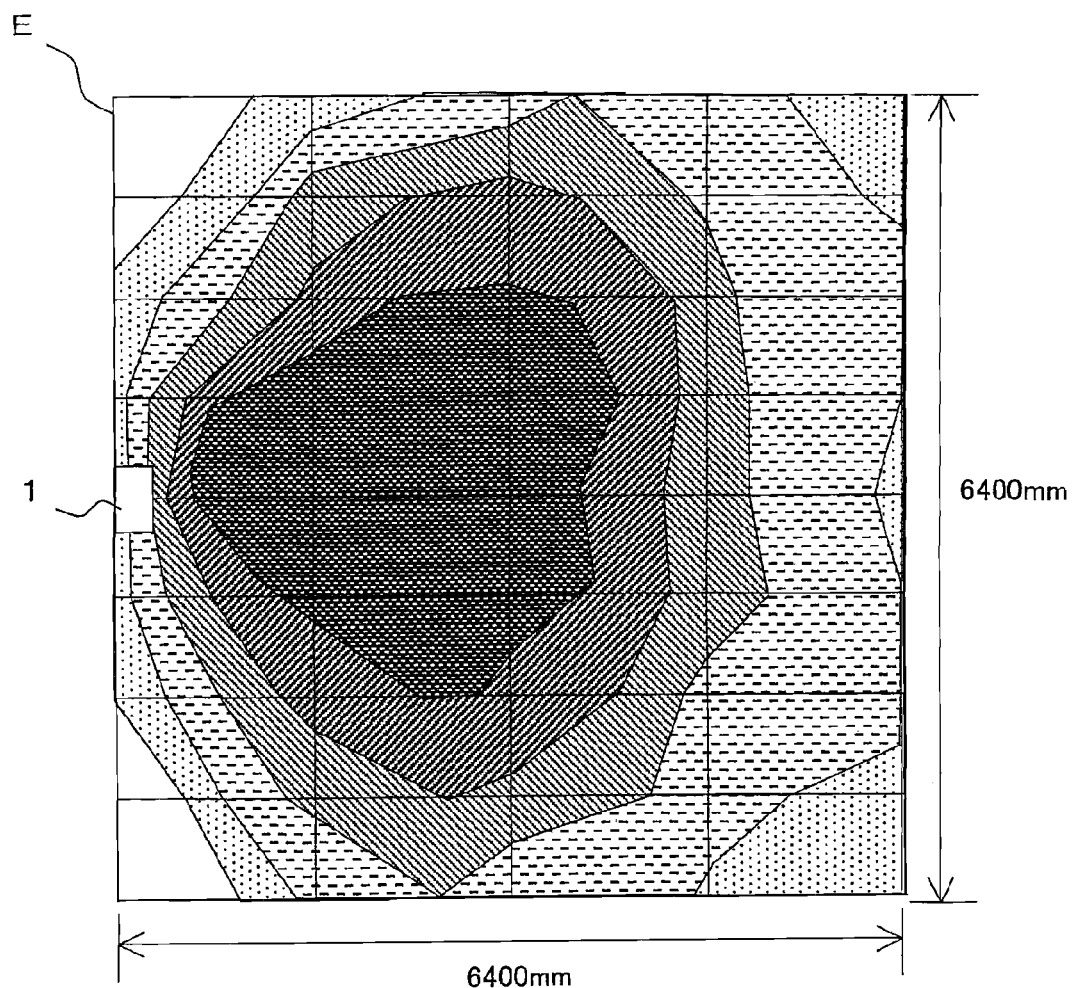
Figure 19:
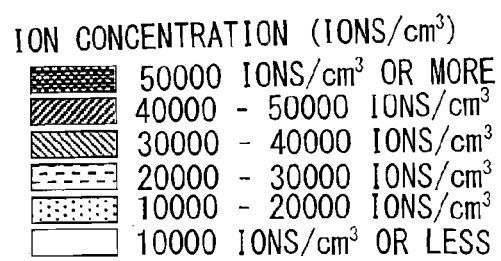
Figure 21:
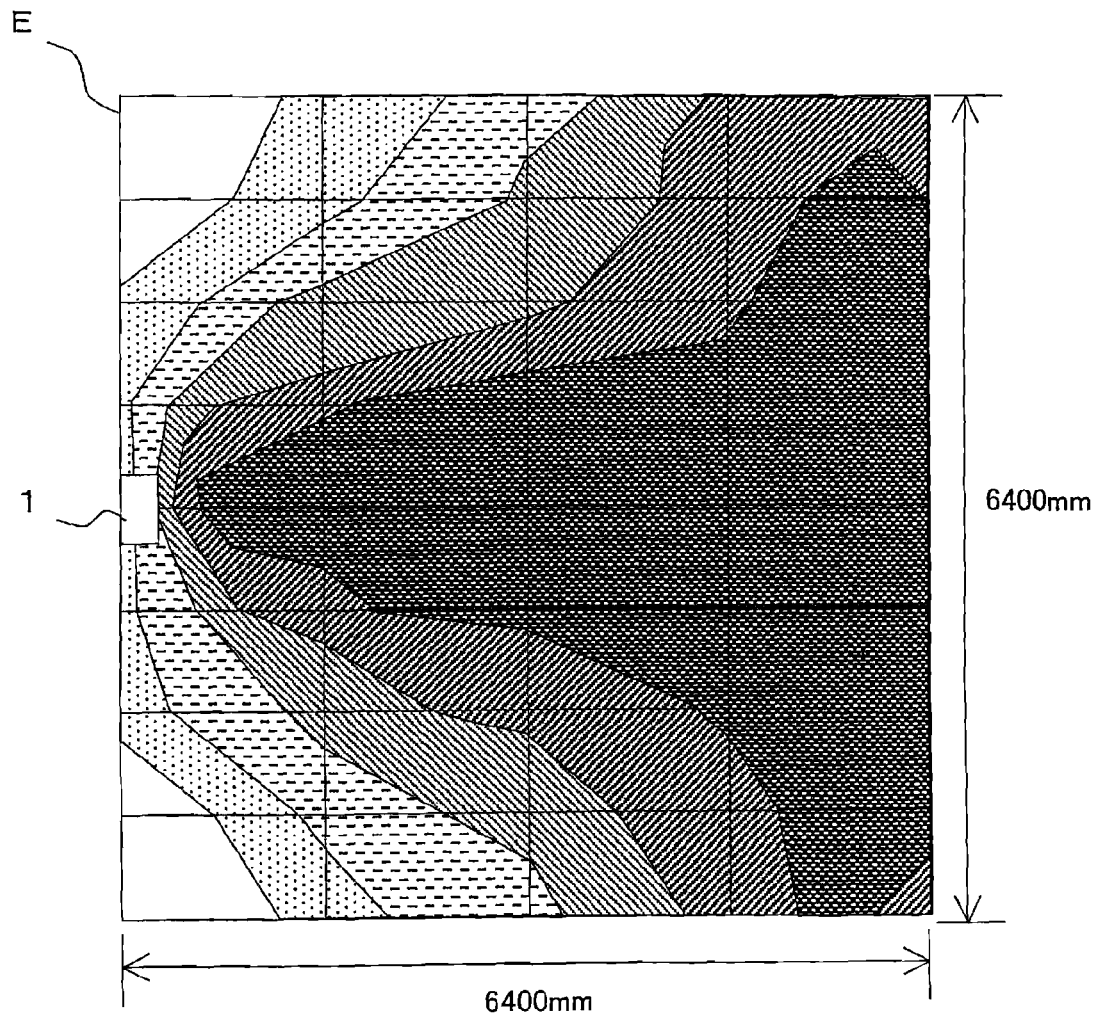
Figure 22:
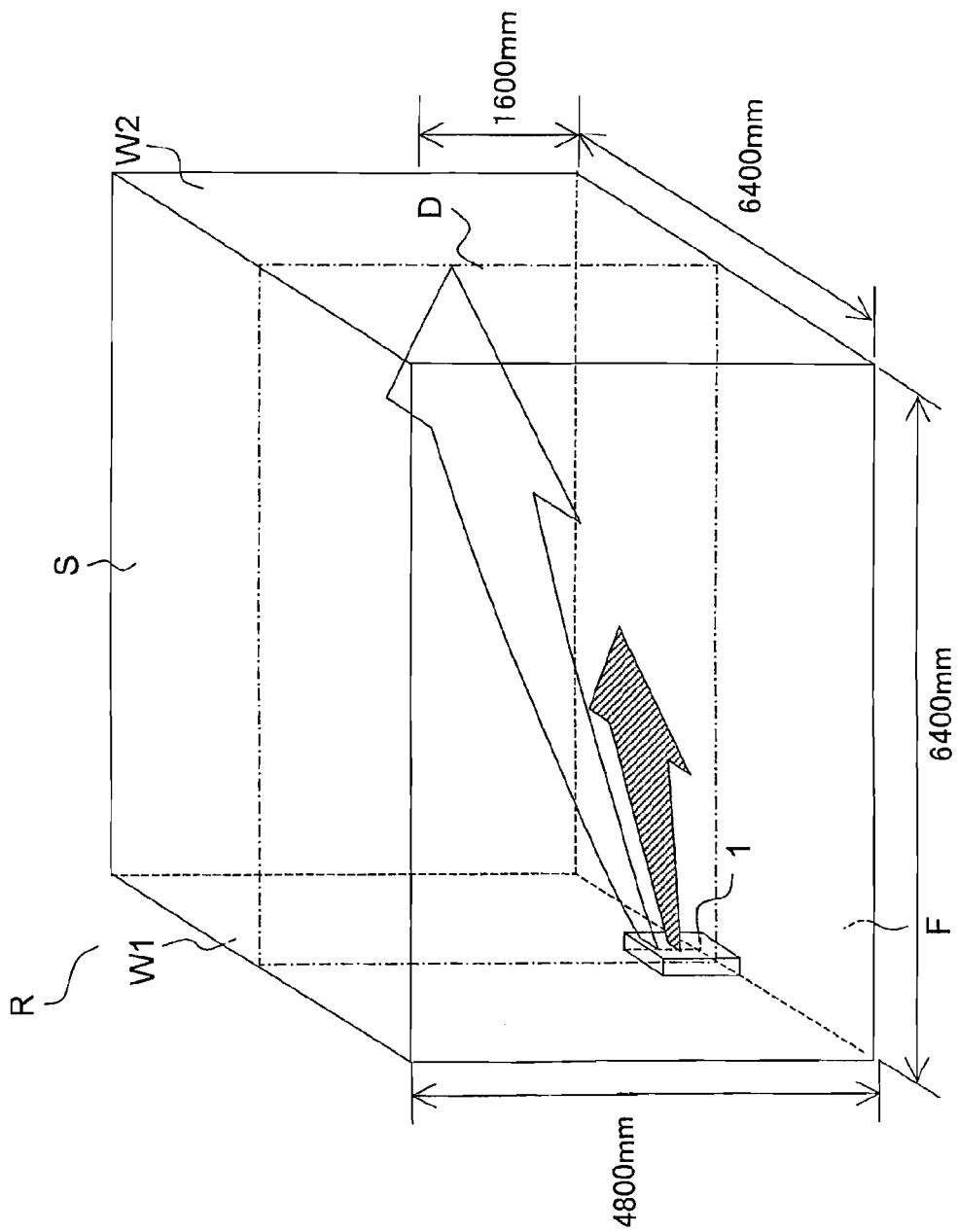
Figure 23:
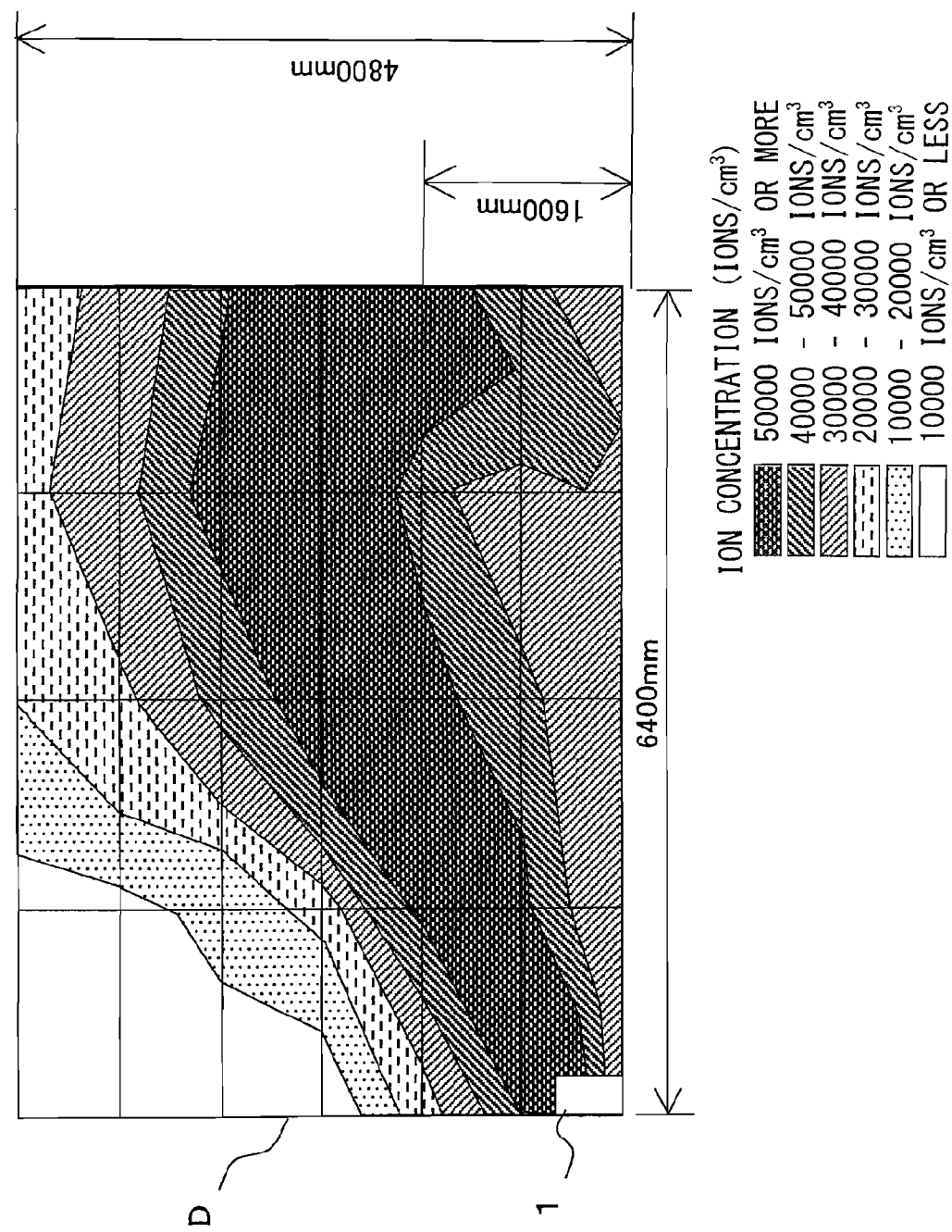
Figure 24:
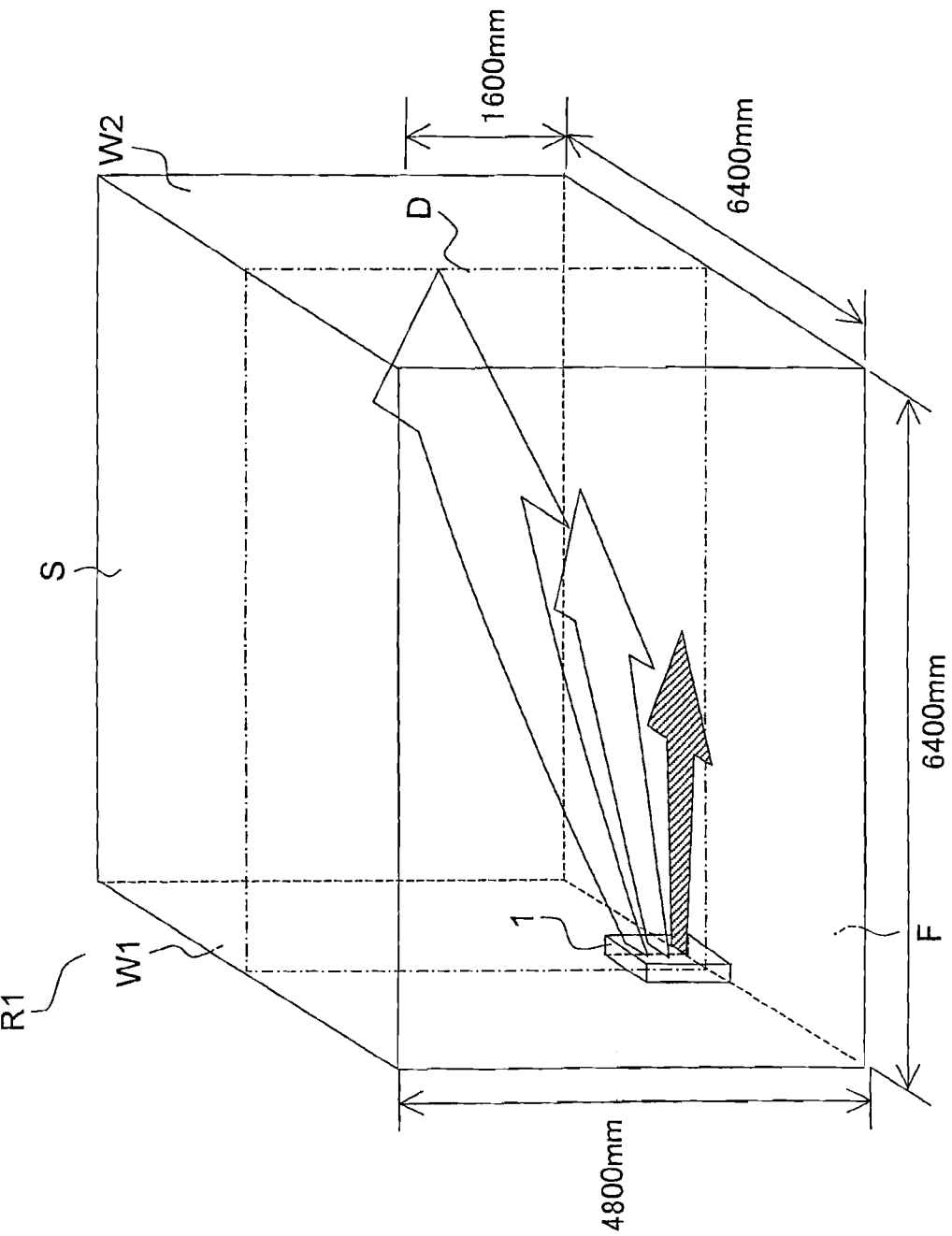
Figure 25:
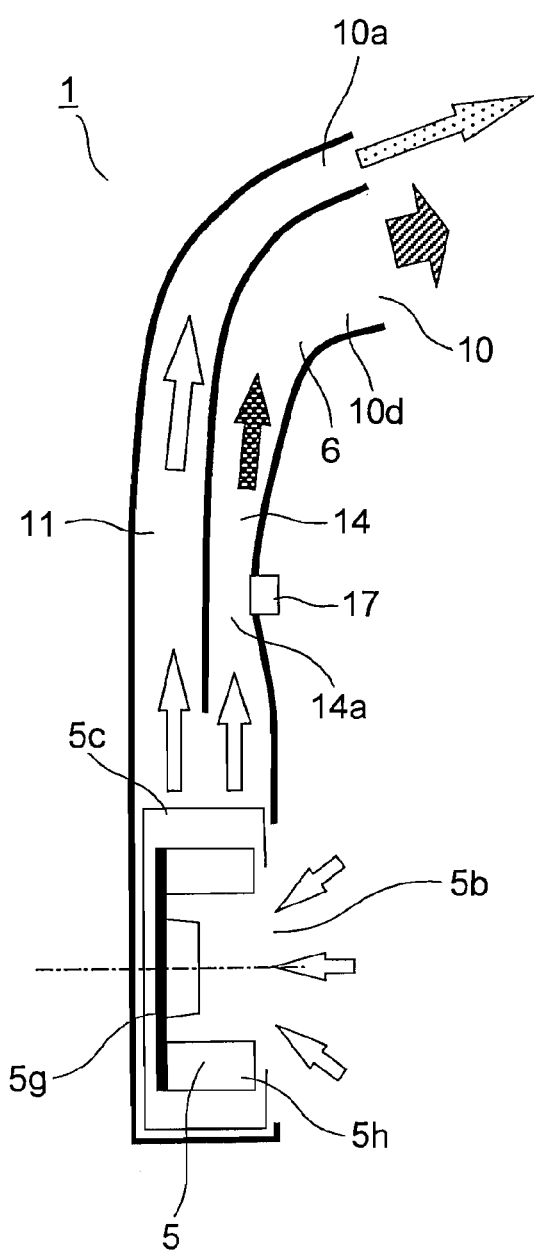
Figure 26:
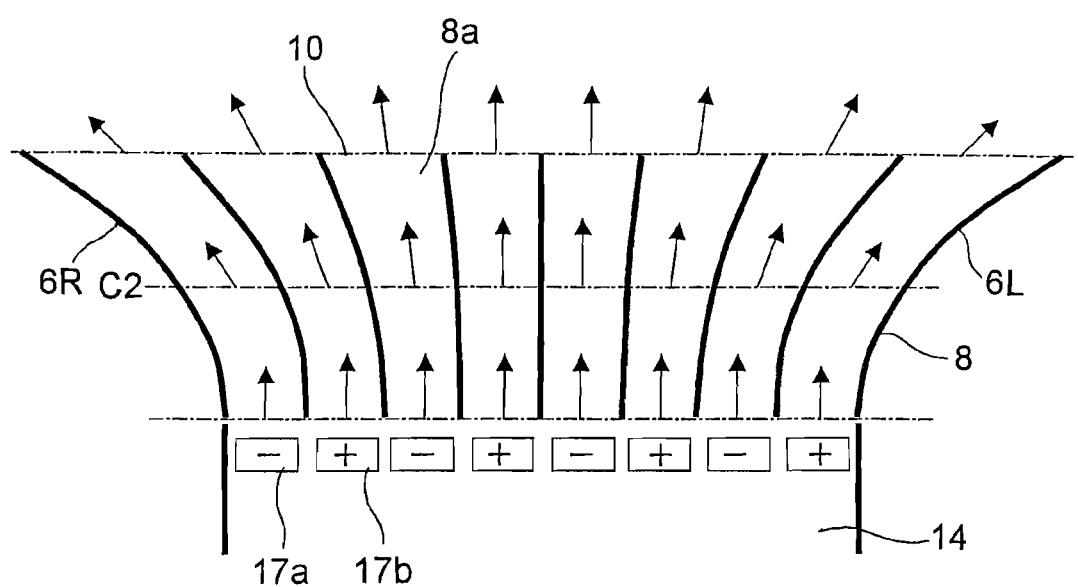
Figure 27:
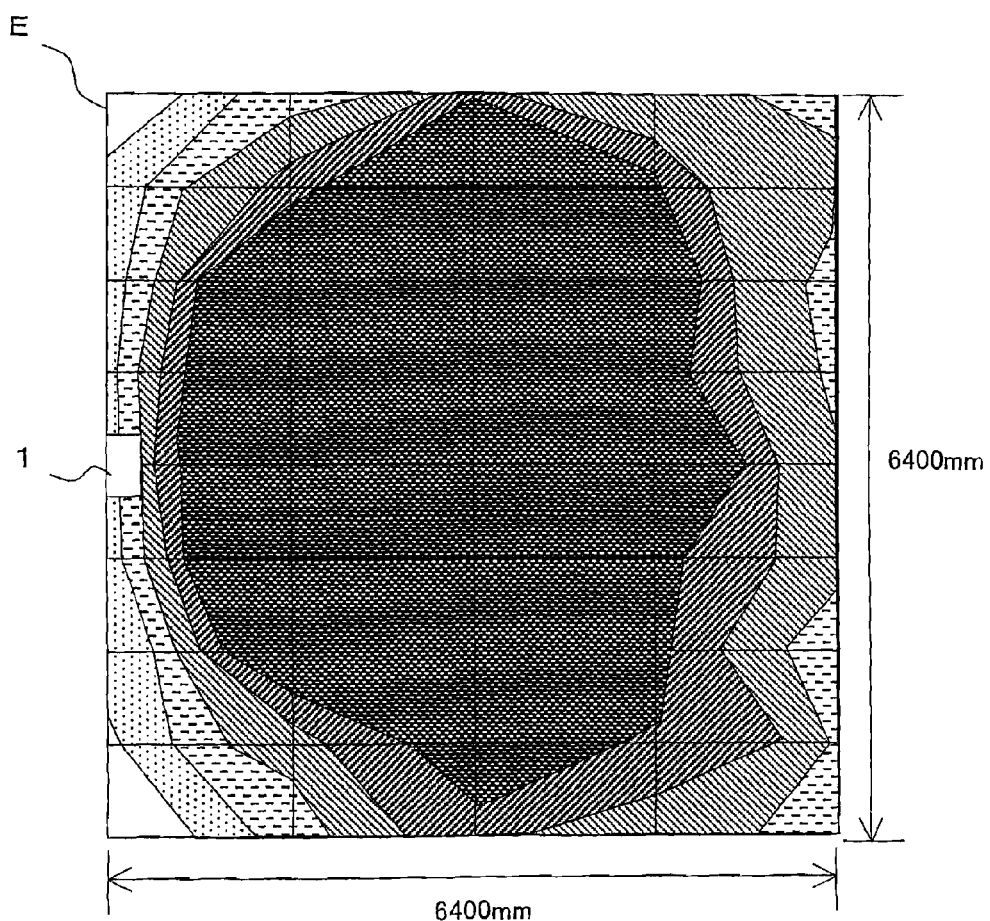
Figure 28:
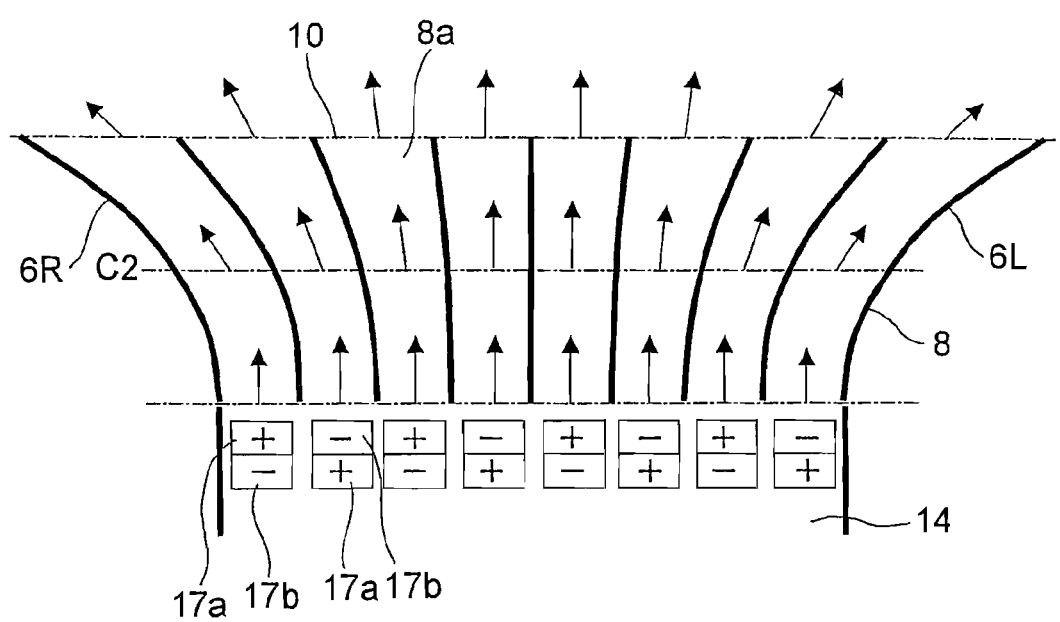

The present invention is characterized in that, in the fine particle diffusion device configured as described above, vertical division passages that divide the air flow path vertically is provided, and the lateral division passages are composed of thin passages that laterally divide the vertical division passages on the side of the outlet. In this configuration, when the air blower fan is driven, air currents flow in the vertical division passages and are smoothed. Then, the ions generated by the fine particle generation device are included in the lateral division passage formed in the downstream portion of the vertical division passage.

The present invention is characterized in that, in the fine particle diffusion device configured as described above, the ion generation device is arranged in one of the vertical division passages at the lower portion, and the speed of an air current flowing in one of the vertical division passages at the upper portion is higher than the speed of an air current flowing in the vertical division passage at the lower portion. In this configuration, the air current flowing in the upper portion of the outlet functions as the air curtain, and the ions included in the air current at the lower portion are supplied to the lower portion of the living room.

Advantages of the Invention

In the present invention, since the concentration of fine particles discharged through the first outlet through which the first air current is discharged upward is lower than that of fine particles discharged through the second outlet through which the second air current is discharged to the space below the first current, the first air current functions as the air curtain, and thus the fine particles included in the second air current are not diffused to the space above the living space. Thus, it is possible to supply a sufficient number of fine particles to the living space. In particular, in a floor or the like where a living room has a high ceiling, the diffusion of fine particles is reduced, and thus it is possible to obtain larger effects.

In the present invention, since the air flow path includes a plurality of vertical division passages that vertically divide the outlet, and the speed of the air current flowing in the vertical division passage at the upper portion is higher than that of the air current flowing in the vertical division at the lower portion, the air current is discharged through the vertical division passage at the upper portion to the space above the living space, and thus the air current functions as the air curtain, with the result that the diffusion of the air current discharged through the vertical division passage at the lower portion is reduced. Hence, the fine particles discharged to the living space are not diffused to the space above the living space, and thus it is possible to supply a sufficient number of fine particles to the living space.

In the present invention, since the lateral division passages are provided in the laterally extending air flow path, and one of the positive ion and the negative ion flows in each of the lateral division passages, it is possible to reduce the collision of ions resulting from the air current curving and flowing in the air flow path. It is therefore possible to reduce the destroying of the ions, supply a sufficient number of ions into the living room and enhance the sterilization performance.

BRIEF DESCRIPTION OF DRAWINGS

FIG. 1 A perspective view showing a fine particle diffusion device according to a first embodiment of the present invention;

FIG. 2 A side cross-sectional view showing the fine particle diffusion device according to the first embodiment of the present invention;

FIG. 3 A side cross-sectional view showing an air flow path of the fine particle diffusion device according to the first embodiment of the present invention;

FIG. 4 A side cross-sectional view illustrating the function of vertical division passages of the air flow path of the fine particle diffusion device according to the first embodiment of the present invention;

FIG. 5 A side cross-sectional view illustrating the function of the vertical division passages of the air flow path of the fine particle diffusion device according to the first embodiment of the present invention;

FIG. 6 A side cross-sectional view illustrating the function of the vertical division passages of the air flow path of the fine particle diffusion device according to the first embodiment of the present invention;

FIG. 7 A side cross-sectional view illustrating the function of the vertical division passages of the air flow path of the fine particle diffusion device according to the first embodiment of the present invention;

FIG. 8 A plan view showing a laterally increasing width portion of the air flow path of the fine particle diffusion device according to the first embodiment of the present invention;

FIG. 9 A side cross-sectional view illustrating the speed of air flowing in the air flow path of the fine particle diffusion device according to the first embodiment of the present invention;

FIG. 10 A side cross-sectional view illustrating the speed of air flowing in the air flow path of the fine particle diffusion device according to the first embodiment of the present invention;

FIG. 11 A perspective view showing the state of air flowing in a living room with the fine particle diffusion device according to the first embodiment of the present invention;

FIG. 12 A diagram showing results obtained by measuring the concentration of ions on a vertical surface with the fine particle diffusion device according to the first embodiment of the present invention;

FIG. 13 A diagram showing results obtained by measuring the concentration of ions on a horizontal surface with the fine particle diffusion device according to the first embodiment of the present invention;

FIG. 14 A perspective view showing the state of air flowing in the living room with the fine particle diffusion device of comparative example 1 of the present invention;

FIG. 15 A diagram showing results obtained by measuring the concentration of ions on a vertical surface with the fine particle diffusion device of comparative example 1 of the present invention;

FIG. 16 A perspective view showing the state of air flowing in the living room with the fine particle diffusion device of comparative example 2 of the present invention;

FIG. 17 A diagram showing results obtained by measuring the concentration of ions on a vertical surface with the fine particle diffusion device of comparative example 2 of the present invention;

FIG. 18 A plan view showing the state of air flowing in the living room with the fine particle diffusion device of comparative example 3 of the present invention;

FIG. 19 A diagram showing results obtained by measuring the concentration of ions on a horizontal surface with the fine particle diffusion device of comparative example 3 of the present invention;

FIG. 20 A plan view showing the state of air flowing in the living room with the fine particle diffusion device of comparative example 4 of the present invention;

FIG. 21 A diagram showing results obtained by measuring the concentration of ions on a horizontal surface with the fine particle diffusion device of comparative example 4 of the present invention;

FIG. 22 A perspective view showing the state of air flowing in the living room with a fine particle diffusion device according to a second embodiment of the present invention;

FIG. 23 A diagram showing results obtained by measuring the concentration of ions on a vertical surface with the fine particle diffusion device according to the second embodiment of the present invention;

FIG. 24 A perspective view showing the state of air flowing in the living room with a fine particle diffusion device according to a third embodiment of the present invention;

FIG. 25 A side cross-sectional view showing a fine particle diffusion device according to a fourth embodiment of the present invention;

FIG. 26 A plan view showing a laterally increasing width portion of an air flow path of a fine particle diffusion device according to a fifth embodiment of the present invention;

FIG. 27 A diagram showing results obtained by measuring the concentration of ions on a horizontal surface with the fine particle diffusion device according to the fifth embodiment of the present invention; and FIG. 28 A plan view showing a laterally increasing width portion of an air flow path of a fine particle diffusion device according to a sixth embodiment of the present invention.

BEST MODE FOR CARRYING OUT THE INVENTION

Figure 1:
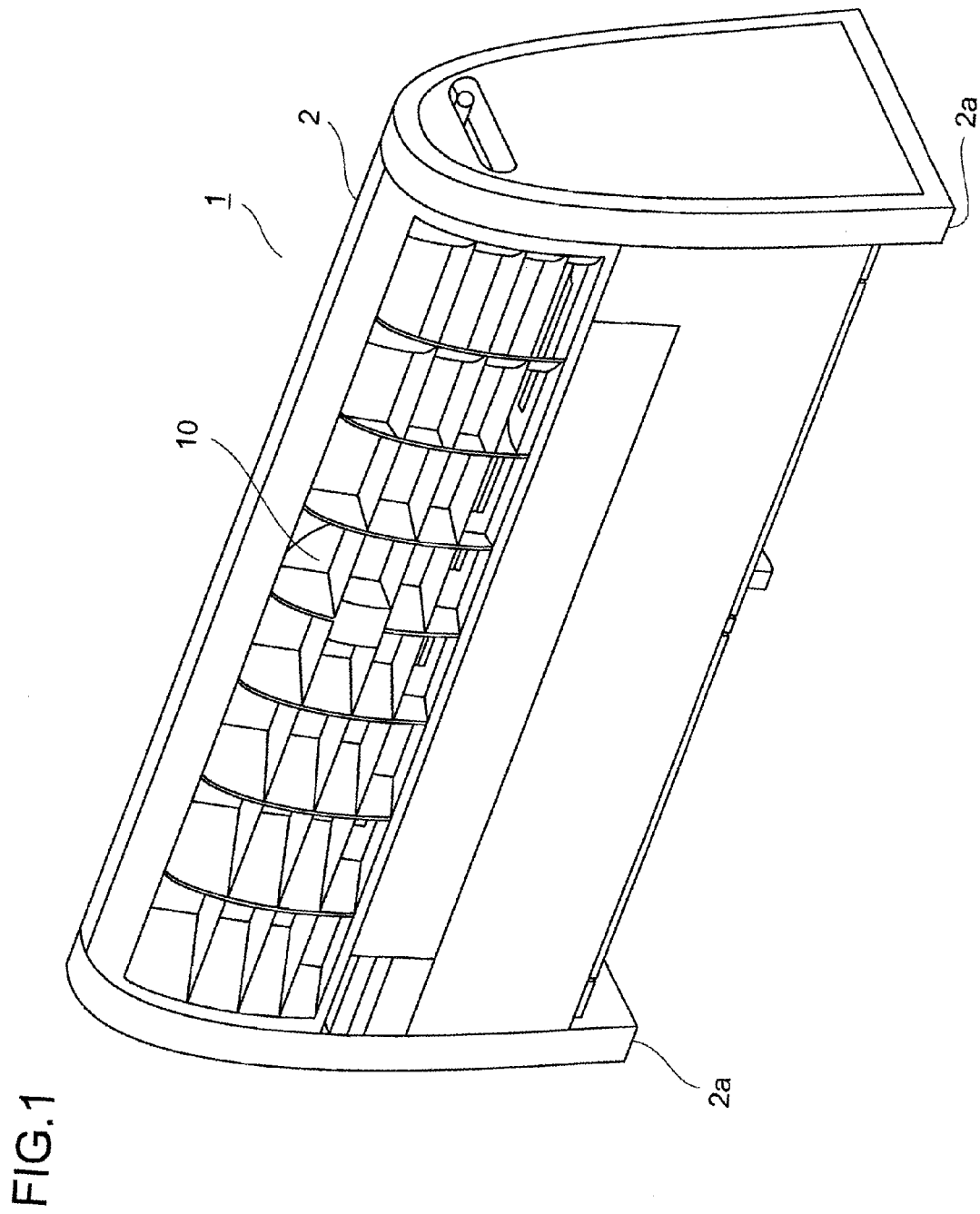

Embodiments of the present invention will be described below with reference to the accompanying drawings. FIG. 1 is an external perspective view showing a fine particle diffusion device of a first embodiment. The fine particle diffusion device 1 is formed with an ion diffusion device that diffuses and discharges ions. The fine particle diffusion device 1 is provided with leg portions 2a at the left and right ends of a main body enclosure 2, and is placed on the floor surface of a living room. An outlet 10 is opened in an upper portion of the front surface of the main body enclosure 2.

Figure 2:
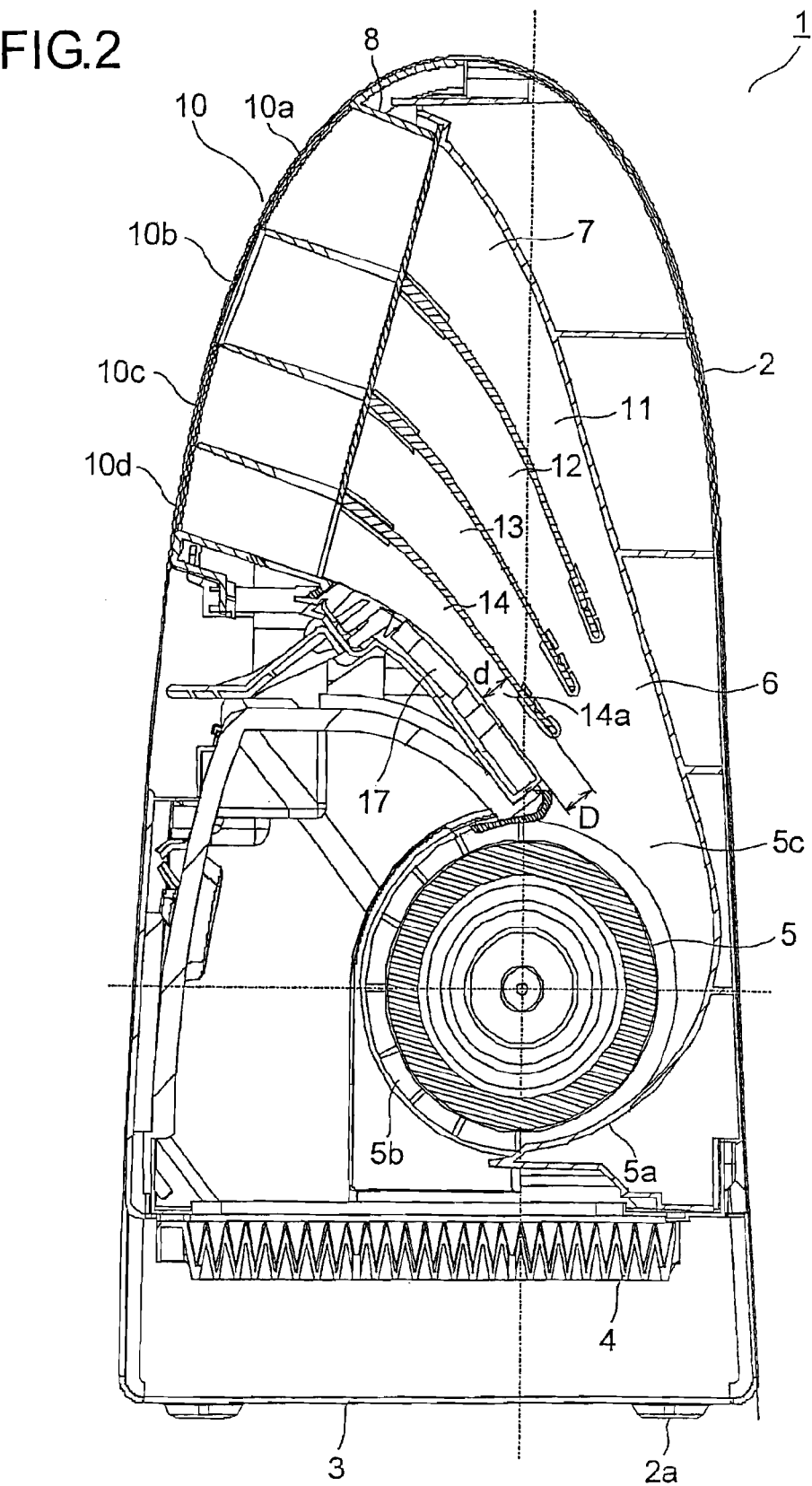

FIG. 2 shows a side cross-sectional view of the fine particle diffusion device 1.

In the bottom surface of the main body enclosure 2, an inlet 3 through which air within the living room is sucked is provided. In a lower portion of the main body enclosure 2, a blower fan 5 covered by a housing 5a is provided. The blower fan 5 is formed with a cross flow fan; air is sucked into the housing 5a in a circumferential direction of a rotor (not shown) through an air intake port 5b, and the air is discharged through an air outlet port 5c in the circumferential direction. An air filter 4 is provided between the inlet 3 and the blower fan 5.

The air outlet port 5c of the blower fan 5 and the outlet 10 are coupled to each other by an air flow path 6 in which an air current blown by the blower fan 5 flows. The air flow path 6 is formed integrally with the housing 5a, and extends upward and bends frontward. In the air flow path 6, a plurality of vertical division passages 11 to 14 (division passages) that are divided in a vertical direction are sequentially arranged from top to bottom.

The vertical division passage 11 at the top is arranged in the outer circumferential side of the air outlet port 5c of the blower fan 5; the vertical division passage 14 at the bottom is arranged in the inner circumferential side of the air outlet port 5c of the blower fan 5. The inner circumferential side of the air outlet port 5c indicates the front of the rotational direction of the rotor, and is the side of a lower wall 6D (see FIG. 3). The outer circumferential side of the outlet port 5c indicates the back of the rotational direction of the rotor, and is the side of an upper wall 6U (see FIG. 3). The speed of an air current in the outer circumferential side of the air outlet port 5c is higher than that of an air current in the inner circumferential side due to a centrifugal force.

The outlet 10 is vertically divided into openings 10a, 10b, 10c and 10d according to the vertical division passages 11 to 14. As described in detail later, a vertically increasing width portion 7 is provided in each of the vertical division passages 11 to 14 in the upstream side; a laterally increasing width portion 8 is provided in the downstream side.

In the vertical division passage 14 at the lowermost part, electrodes 17a and 17b (first and second ion generation portions; see FIG. 8) of a fine particle generation device 17 are so arranged as to be exposed. A voltage having an alternating-current waveform or an impulse waveform is applied to the electrodes 17a and 17b of the fine particle generation device 17. A positive voltage is applied to the electrode 17a, and ions generated by ionization combine with water in the air to form positive cluster ions composed mainly of $H^+(H_2O)m$.

A negative voltage is applied to the electrode 17b, and ions generated by ionization combine with water in the air to form negative cluster ions composed mainly of $O_2^-(H_2O)n$. Here, m and n each represent a whole number. $H^+(H_2O)m$ and $O_2^-(H_2O)n$ aggregate on the surfaces of airborne bacteria in the air, smelling components and surface colonized bacteria in storage materials, and surround them.

As shown in formulas (1) to (3), collisions occur to form and aggregate hydroxyl radicals (.OH), which are active species, and hydrogen peroxide ($H_2O_2$) on the surfaces of microorganisms and the like, and thus airborne bacteria, smelling components and the like are destroyed. Here, m' and n' each represent a whole number. Hence, positive ions and negative ions are generated and discharged through the outlet 10, and thus it is possible to sterilize a room and remove smells.

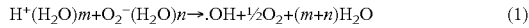

$$H^+(H_2O)m + O_2^-(H_2O)n \rightarrow \cdot OH + \tfrac{1}{2}O_2 + (m+n)H_2O \qquad (1)$$

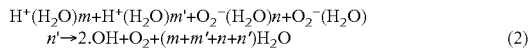

$$H^+(H_2O)m + H^+(H_2O)m' + O_2^-(H_2O)n + O_2^-(H_2O)n' \rightarrow 2 \cdot OH + O_2 + (m+m'+n+n')H_2O \qquad (2)$$

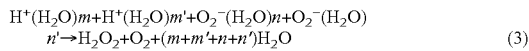

$$H^+(H_2O)m + H^+(H_2O)m' + O_2^-(H_2O)n + O_2^-(H_2O)n' \rightarrow H_2O_2 + O_2 + (m+m'+n+n')H_2O \qquad (3)$$

It is conventionally known that positive ions $H^+(H_2O)m$ and negative ions $O_2^-(H_2O)n$ are discharged into the air and the reactions of the ions kill airborne bacteria and the like. Since these ions recombine with each other to destroy themselves, even if a high concentration can be achieved near the electrodes of an ion generation element, the concentration is rapidly reduced as the ions are discharged further.

Hence, although an ion concentration of a few tens of thousands of ions per $cm^3$ can be achieved in a small volume space such as an experimental device, an ion concentration of at most a few thousands of ions per $cm^3$ can be achieved in a large space such as an actual living space or working space.

On the other hand, in an experiment, 99% of avian influenza viruses are removed in ten minutes at the time of an ion concentration of 7000 ions per $cm^3$, and 99.9% thereof are removed in ten minutes at the time of an ion concentration of 50000 ions per $cm^3$. In other words, when viruses are assumed to be present in the air at a rate of 1000 viruses per $cm^3$, as a result of the sterilization using the ions, viruses are left at a rate of 10 viruses per $cm^3$ and at a rate of one virus per $cm^3$ in above cases, respectively. Hence, when the ion concentration is increased from 7000 ions per $cm^3$ to 50000 ions per $cm^3$, the remaining viruses can be reduced to one-tenth.

Therefore, in order to prevent infectious diseases and achieve environmental cleanup, it is very important not only to discharge the ions but also to keep high the ion concentration in an entire living space or working space where people live.

Figure 3:
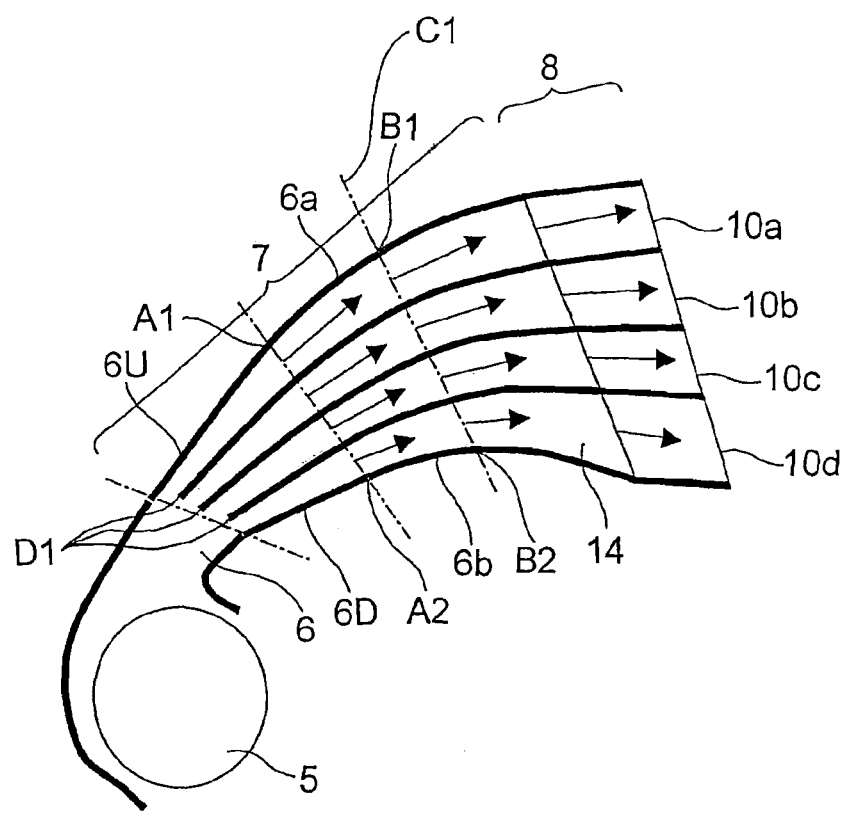

FIG. 3 is a side cross-sectional view schematically showing the configuration of the air flow path 6. The upper wall 6U and the lower wall 6D of the air flow path 6 have curved surface portions 6a and 6b, respectively. Individual wall surfaces that form the vertical division passages 11 to 14 are curved along the upper wall 6U and the lower wall 6D; one ends D1 thereof are provided near the blower fan 5.

Thus, the vertical division passages 11 to 14 are formed to extend from the vicinity of the blower fan 5 to the outlet 10. The starting points A1 and A2 of the curved surface portions 6a and 6b are arranged downstream from the starting point (D1) of the vertical division passages 11 to 14. Thus, a line C1 intersecting the centers of the curved surface portions 6a and 6b is arranged downstream from the starting point (D1) of the vertical division passages 11 to 14.

When an air current flowing in an upper portion of the air flow path 6 is bent frontward by the curved surface portions 6a and 6b, the air current moves upward due to the inertia thereof, and thus the air current is more likely to move apart from the lower wall 6D and along the upper wall 6U. Therefore, the speed of the air current flowing in the upper portion of the air flow path 6 is higher than that of an air current flowing in a lower region.

Moreover, the vertical division passages 11 to 14 are sequentially arranged from the outer circumferential side of the air outlet port 5c of the blower fan 5. Thus, it is possible to stepwise increase the speeds of air currents flowing in the vertical division passages 11 to 14 from the vertical division passage on the top.

When the vertical division passages 11 to 14 are not provided, the amount of air current separating from the lower wall 6D is increased. Hence, as shown in FIG. 4, in the speed distribution of air currents around the outlet 10, a backward current region H where air currents are reversed in the side of the lower wall 6D is produced, and the air currents are disturbed.

Figure 5:
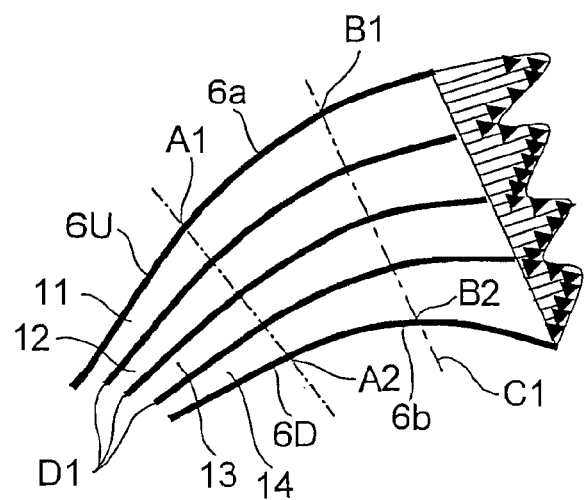
Figure 6:
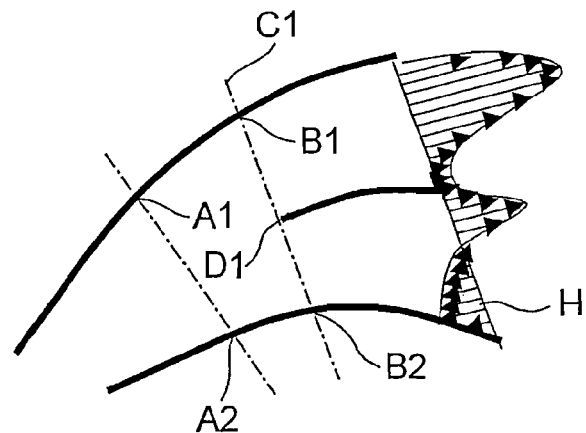

The vertical division passages 11 to 14 are provided to extend from the vicinity of the blower fan 5; the wetted perimeter (a perimeter surrounding a cross section) of the cross section of a flow path is increased due to the vertical division passages 11 to 14. Hence, the air currents are affected more by the viscosity than by the inertia, and thus the air currents are more likely to move along the wall surfaces of the vertical division passages 11 to 14. In this way, as shown in FIG. 5, no backward current region H is formed, and thus the separation of the air currents is reduced and the air currents are prevented from being disturbed Here, when the starting point (D1) of the division passage is arranged downstream from the line C1 intersecting the centers B1 and B2 of the curved surface portions 6a and 6b, as shown in FIG. 6, a backward current region H is formed. Hence, when the line C1 intersecting the centers of the curved surface portions 6a and 6b is arranged downstream from the starting point (D1) of the vertical division passages 11 to 14, it is possible to prevent the air currents from being disturbed. When the starting point (D1) of the vertical division passages 11 to 14 is arranged near the air outlet port 5c of the blower fan 5, it is possible to reliably prevent the air currents from being disturbed.

Here, when the curvature of the curved surface portions 6a and 6b is constant, centers B1 and B2 are the center points of creepage distances. When the curvature of the curved surface portions 6a and 6b are changed, and angles formed between horizontal lines and tangents at the starting point and the end point of the curved surface portions 6a and 6b are assumed to be $\theta 1$ and $\theta 2$, respectively, the centers B1 an B2 are positions that satisfy $(\theta 1 + \theta 2)/2$.

Figure 4:
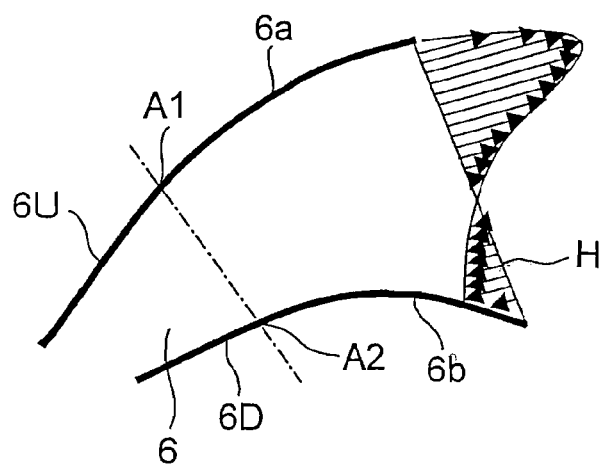
Figure 7:
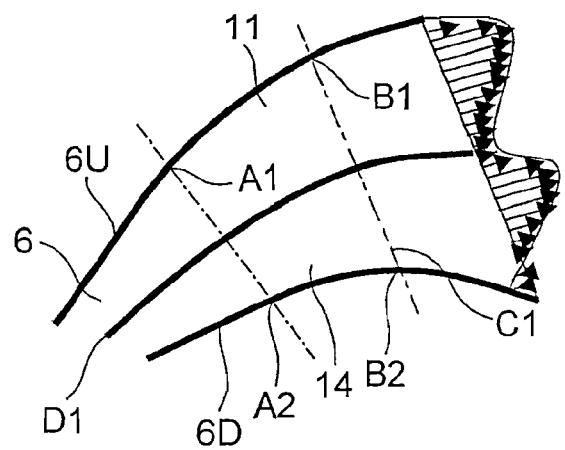

Even when, as shown in FIG. 7, two vertical division passages 11 and 14 are provided, it is possible to reduce the disturbance of air currents as compared with the cases shown in FIGS. 4 and 6. Here, a backward current region H may be formed in part of the air flow path 6 depending on the curvature of the air flow path 6. On the other hand, when the number of division passages is increased, a pressure loss is increased. Therefore, the number of division passages is set according to the area of the flow path of and the curvature of the air flow path 6.

As shown in FIG. 3, in the vertically increasing width portion 7, the distance between the upper wall 6U and the lower wall 6D of the air flow path 6 is increased in a vertical direction as the air flow path 6 extends from the upstream side to the down stream side. Thus, the air currents are discharged through the outlet 10 such that they extend in the vertical direction. The width of each of the vertical division passages 11 to 14 is increased in the vertical direction as they extend from the upstream side to the down stream side; the cross section of the flow path is formed in the shape of a slit in which its lateral width is sufficiently greater than its width in a height direction. Hence, the areas of portions of the upper and lower wall surfaces of the vertical division passages 11 to 14 in contact with the air currents flowing in the air flow path 6 are increased. It is therefore possible to extend the air currents flowing in the vertical division passages 11 to 14 in the vertical direction without the air currents separating from the upper and lower wall surfaces.

Figure 8:
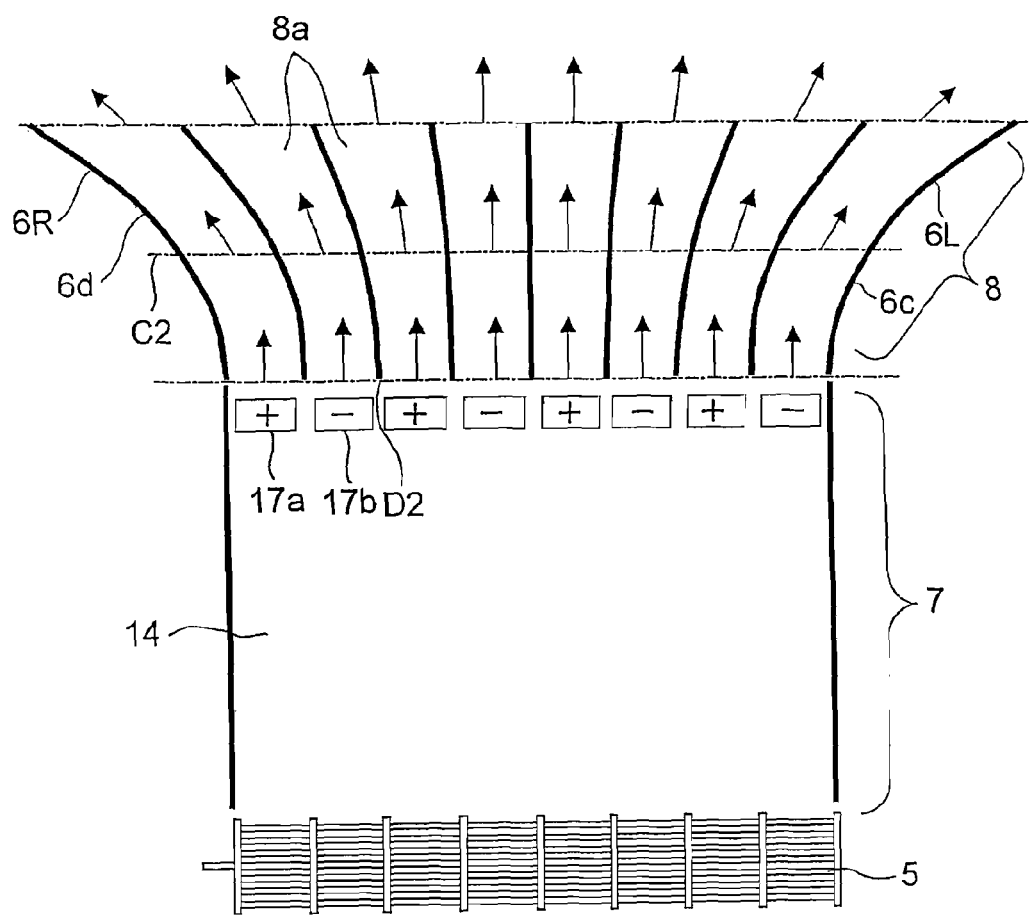

The laterally increasing width portion 8 is arranged downstream from the vertically increasing width portion 7; the upper and lower wall surfaces thereof are extended along a plane from the edge of the vertically increasing width portion 7. FIG. 8 shows a plan view of the vertical division passage 14. In the laterally increasing width portion 8, the distance between a left wall 6L and a right wall 6R of the air flow path 6 is increased in the lateral direction as the air flow path 6 extends from the upstream side to the down stream side. Thus, the air currents are discharged through the outlet 10 such that they extend in the lateral direction.

The laterally increasing width portion 8 has lateral division passages 8*a* that are composed of a plurality of thin passages obtained by further dividing the vertical division passages 11 to 14 in the lateral direction. The electrodes 17*a* and 17*b* of the fine particle generation device 17 are provided near the open ends of the lateral division passages 8*a* on the air inflow side. Hence, positive ions generated at the electrode 17*a* flow in one of the lateral division passages 8*a*. Negative ions generated at the electrode 17*b* flow in one of the lateral division passages 8*a* adjacent to the above-mentioned lateral division passage 8*a*. Thus, it is possible to reduce the destroying of the positive and negative ions resulting from the positive and negative ions colliding with each other.

The left wall 6L and the right wall 6R have curved surface portions 6*c* and 6*d*. Individual wall surfaces that form the lateral division passages 8*a* are curved along the left wall 6L and the right wall 6R. The width of each of the lateral division passages 8*a* between the left and right wall surfaces is increased in the lateral direction as the lateral division passage 8*a* extends from the upstream side to the downstream side; the lateral width of the cross section of the flow path is narrowed with respect to the vertically increasing width portion 7. Thus, the areas of portions of the left and right wall surfaces in contact with the air currents flowing in the air flow path 6 are increased. It is therefore possible to extend the air currents flowing in the lateral division passages 8*a* in the lateral direction without the air currents separating from the left and right wall surfaces.

A line C2 intersecting the centers of the curved surface portions 6*c* and 6*d* is arranged downstream from one ends D2 of the wall surfaces of the lateral division passages 8*a*. In other words, the open ends of the lateral division passages 8*a* on the air inflow side are arranged upstream from the line C2. It is therefore possible to reliably curve the air currents along the lateral division passages 8*a* and prevent the disturbance of the air currents in the laterally increasing width portion 8 resulting from the separation of the air currents.

The laterally increasing width portion 8 may be arranged upstream from the vertically increasing width portion 7. Here, the air flow path 6 has the lateral division passages divided in the lateral direction; the laterally increasing width portion 8 is formed upstream from the lateral division passages. The width of the laterally increasing width portion 8 is increased in the lateral direction as the laterally increasing width portion 8 extends from the upstream side to the downstream side. In the vertically increasing width portion 7 arranged downstream from the lateral division passages, the vertical division passages are formed with thin passages obtained by further dividing the lateral division passages in the vertical direction. The width of each of the vertical division passages is increased in the vertical direction as the vertical division passage extends from the upstream side to the downstream side.

However, the laterally increasing width portion 8 is more preferably arranged downstream from the vertically increasing width portion 7. Thus, the air flow path 6 integral with the housing 5*a* of the blower fan 5 can be formed with a release direction of the vertically increasing width portion 7 being the lateral direction and a release direction of the laterally increasing width portion 8 being the forward and backward direction. It is therefore possible to simply form the air flow path 6.

Figure 9:
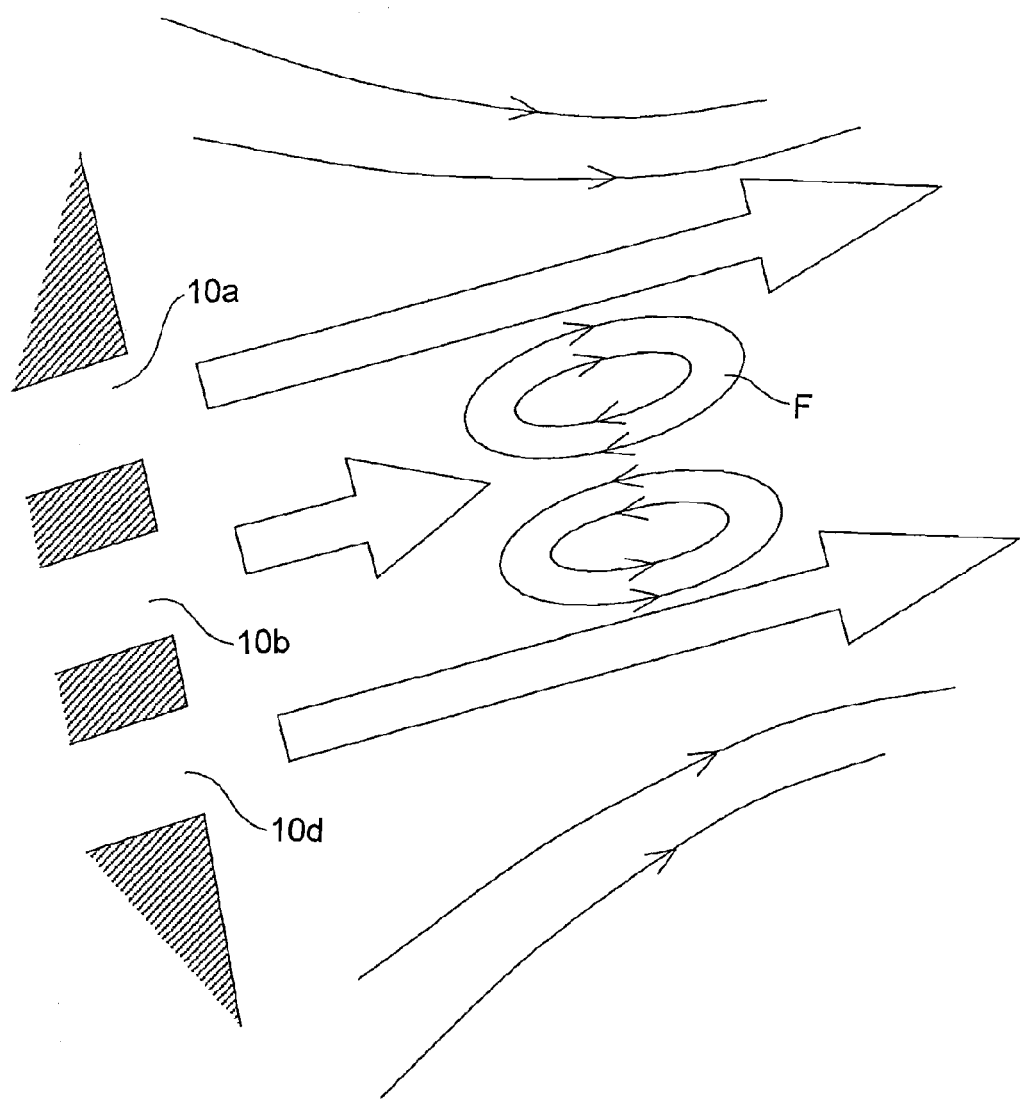
Figure 10:
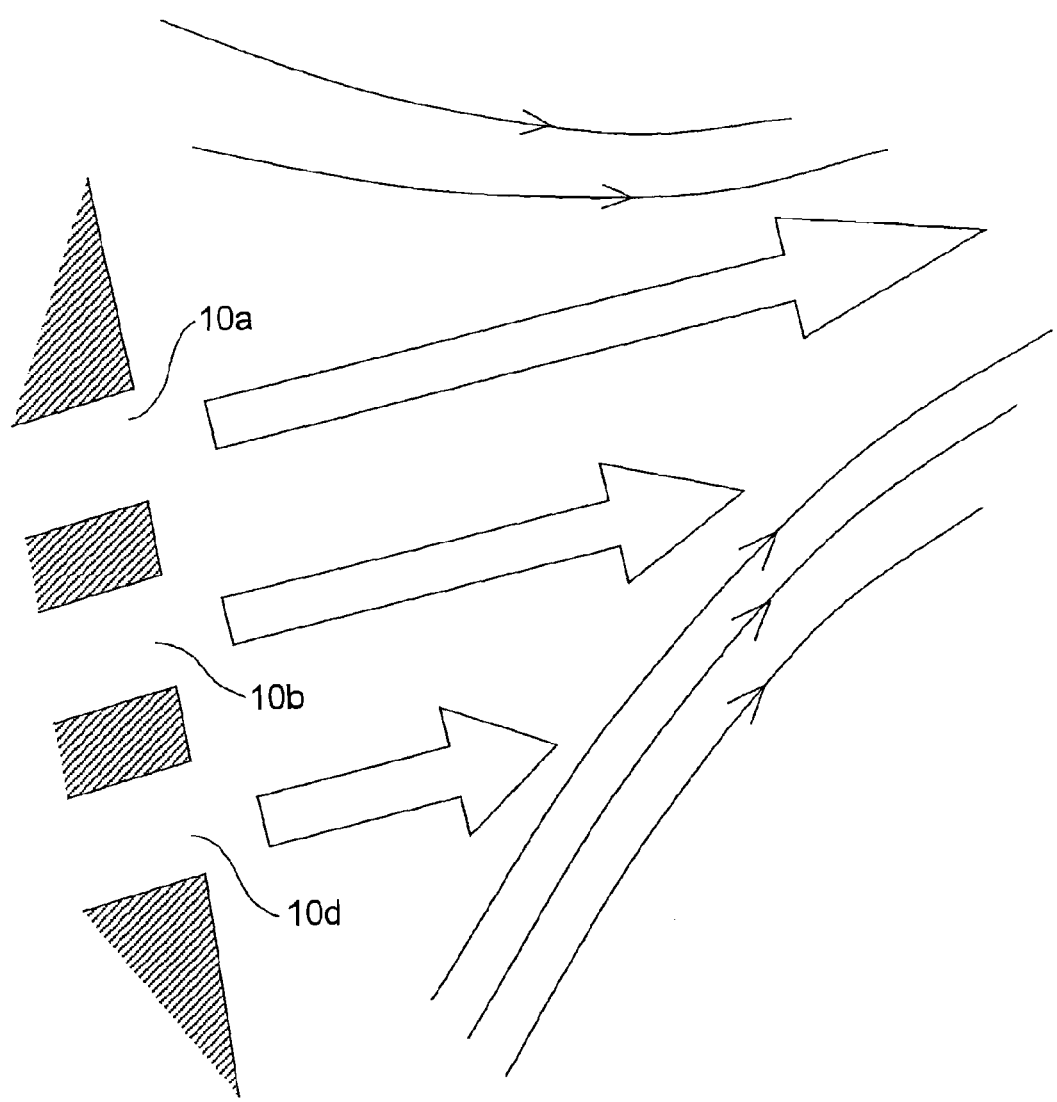

As shown in FIG. 2 described previously, in the vertical division passage 14, a narrowed portion 14*a* is provided upstream from the fine particle generation device 17. The width d of the narrowed portion 14*a* in a height direction is narrower than the width D of the vertical division passage 14 in a height direction at the starting point. With the narrowed portion 14*a*, the speed of air is increased at the fine particle generation device 17 and the air current is smoothed. Thereafter, the flow path is extended by the vertically increasing width portion 7.

When the ion concentration is high and saturation occurs near the electrodes 17*a* and 17*b* of the fine particle generation device 17, it is difficult to generate the ions. Hence, with the narrowed portion 14*a*, it is possible to increase the speed of the air current at the electrodes 17*a* and 17*b* of the fine particle generation device 17 and thus reduce the ion concentration. In this way, it is possible to generate a larger number of ions with the fine particle generation device 17 and incorporate the ions into the air current.

When, in the fine particle diffusion device 1 configured as described above, the blower fan 5 and the fine particle generation device 17 are driven, air within the living room is taken through the inlet 3 into the main body enclosure 2. From the air taken into the main body enclosure 2, dust is filtered by the air filter 4, and the air is guided through air intake port 5*b* to the blower fan 5.

The air discharged from the blower fan 5 flows through the air outlet port 5*c* in the air flow path 6. The air current flowing in the air flow path 6 is divided by vertical division passages 11 to 14; the flow path is extended in the vertical direction in the vertically increasing width portion 7 and is extended in the lateral direction in the laterally increasing width portion 8. Thus, the air current expanded in the vertical and lateral directions is discharged through the outlet 10.

The air current flowing in the vertical division passage 14 at the bottom of the air flow path 6 is divided by the lateral division passages 8*a*. Either the positive ions or the negative ions are incorporated into each of the lateral division passages 8*a* with the electrodes 17*a* and 17*b* in the fine particle generation device 17. Thus, the air current (second air current) including the positive and negative ions is discharged through the opening 10*d* (second outlet).

Since the air currents (first air current) discharged through the openings 10*a*, 10*b* and 10*c* (first outlet) have flowed in the vertical division passages 11 to 13 at the upper portion of the air flow path 6, their speeds are faster. Hence, the air currents discharged through the openings 10*a*, 10*b* and 10*c* function as an air curtain to prevent ions from diffusing upward. Therefore, the air current is discharged through the opening 10*d* to the living space within the living room, the air currents are discharged through the openings 10*a*, 10*b* and 10*c* to a space above the living space and thus it is possible to supply a sufficient number of ions to the living space and obtain high sterilization effects.

The vertical division passages 11 to 14 are sequentially arranged from top to bottom, and thus the speeds of the air currents discharged through the openings 10*a* to 10*d* are stepwise increased from the air current at the top. Thus, it is possible to reduce the disturbance of the air currents. Specifically, when, as shown in FIG. 9, an air current between upper and lower air currents is slower than the upper and lower air currents, eddy currents F are generated to disturb the air current. On the other hand, when, as shown in FIG. 10, the speeds of the air currents are stepwise varied, no eddy currents are generated, and the disturbance of the air current is reduced. FIGS. 9 and 10 illustrate a case where the openings 10b and 10c form one opening.

Figure 11:
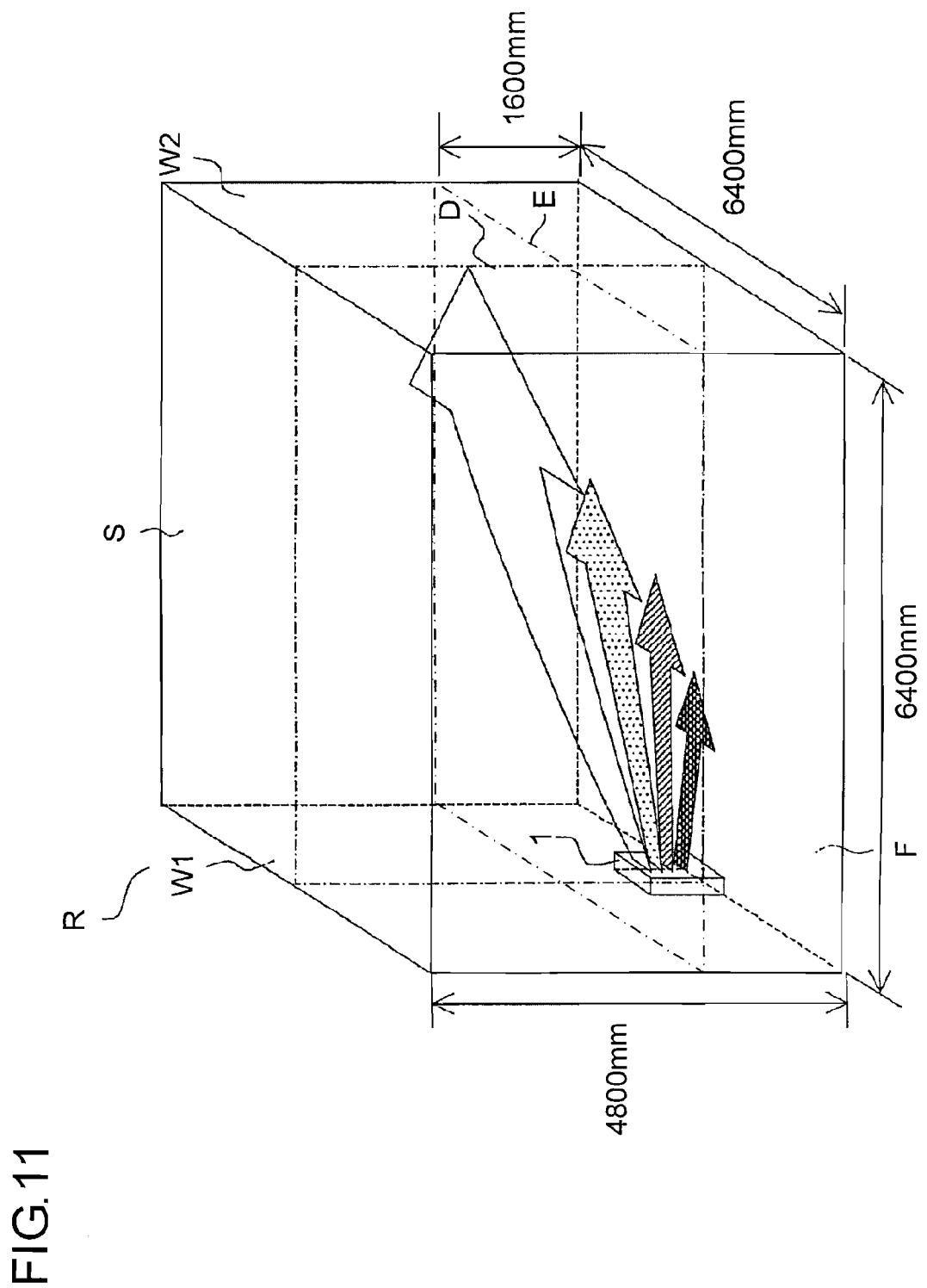
Figure 12:
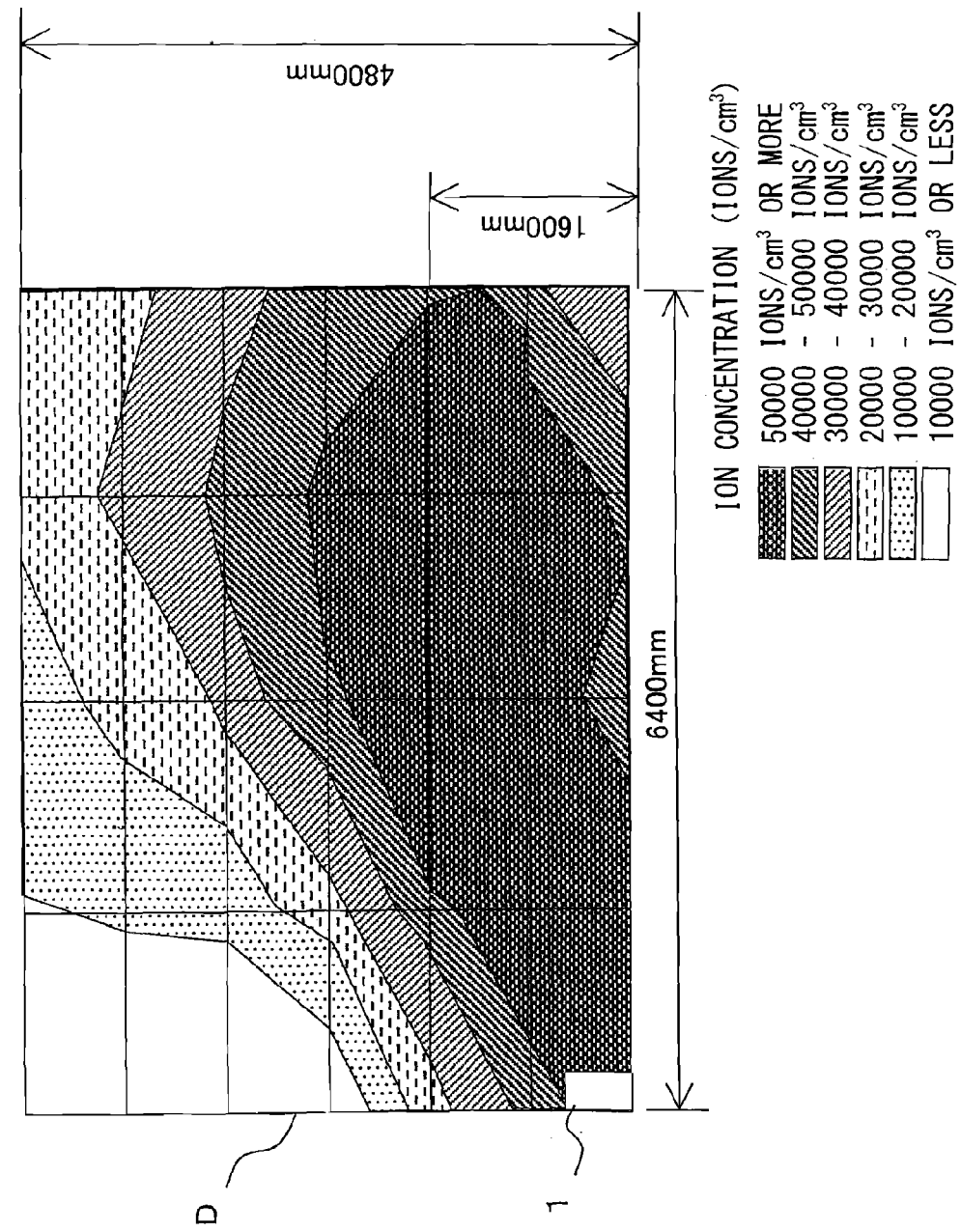

FIGS. 11 to 13 are diagrams showing results obtained by examining the distribution of ions in a living room with the fine particle diffusion device 1 of the present embodiment. The living room R is 4800 mm high, 6400 mm wide and 6400 mm deep. As shown in FIG. 11, the fine particle diffusion device 1 is placed on one side wall W1 and a floor surface F, and discharges, in an obliquely upward direction, an air current toward a side wall W2 opposite the side wall W1.

In FIG. 12, the concentration of ions is measured on a vertical surface D passing through the center of the lateral direction of the fine particle diffusion device 1. In FIG. 13, the concentration of ions is measured on a horizontal surface E at a height of 1600 mm. Since equal numbers of positive ions and negative ions are necessary for sterilization, the concentration of which of the positive ions and the negative ions are fewer in number is shown.

FIGS. 14 and 15 show comparative example 1; when no division passage is formed in the air flow path 6 and an air current is discharged in an obliquely upward direction into the same living room R, the distribution of ions is examined on the vertical surface D. FIGS. 16 and 17 show comparative example 2; when no division passage is formed in the air flow path 6 and an air current is discharged in a vertically upward direction into the same living room R, the distribution of ions is examined on the vertical surface D.

FIGS. 18 and 19 show comparative example 3; when electrodes 17c that simultaneously generate positive and negative ions for the individual lateral division passages 8a are provided, the distribution of ions is examined on the horizontal surface E. In FIG. 18, positive ions and negative ions are included in an air current flowing in each of the lateral division passages 8a. FIGS. 20 and 21 show comparative example 4; when no lateral division passage 8a is provided, the distribution of ions is examined on the horizontal surface E.

FIGS. 15 and 17 show that ions are diffused to a ceiling surface S within the living room R and that the concentration of ions is high in an upper portion of the living room R and the concentration of ions is low in a living space (at a height of 1600 mm or less) in a lower portion of the living room R. On the other hand, in the present embodiment shown in FIG. 12, the upward diffusion of ions is reduced, and thus it is possible to increase the concentration of ions in the living space in the lower portion of the living room R.

In the present embodiment shown in FIG. 13, the destroying of ions is reduced, and thus it is possible to increase the concentration of ions in the middle portion of the living room R. On the other hand, FIG. 19 shows that a region where the concentration of ions is high in the middle portion of the living room R is narrowed. FIG. 21 shows that regions where the concentration of ions is low at the left and right end portions of the living room R are extended and that the region where the concentration of ions is high in the middle portion of the living room R is further narrowed.

In the present embodiment, the openings 10a to 10c (first outlet) through which the air currents (first current) are discharged upward are provided, and the opening 10d (second outlet) through which the air current (second air current) is discharged downward is provided. Ions are included in the air current discharged through the opening 10d; ions are not included in the air currents discharged through the openings 10a to 10c. Hence, the air currents discharged through the openings 10a to 10c function as an air curtain, and thus ions included in the air current discharged through the opening 10d are not diffused to a space above the living space. Thus, it is possible to supply a sufficient number of ions to the living space. In particular, in a floor or the like where a living room has a high ceiling, the diffusion of ions is reduced, and thus it is possible to obtain larger effects.

Part of ions generated by the fine particle generation device 17 may be discharged through the openings 10a to 10c. In this case, when the concentration of ions discharged through the openings 10a to 10c is set lower than the concentration of ions discharged through the opening 10d, as in the case described above, a large number of ions are not diffused to a space above the living space. It is therefore possible to supply a sufficient number of ions to the living space. In particular, in a living room has a low ceiling, a small number of ions are diffused upward, and thus this method is effective.

Since the speeds of the air currents discharged through the openings 10a to 10c are higher than the speed of the air current discharged through the opening 10d, it is possible to reliably form the air curtain. Moreover, since the slow air current is discharged to the living space, it is possible to supply ions to the living space without the wind being sensed by a person. With a plurality of blower fans, air currents having different speeds may be formed.

Since the air current discharged through the opening 10d is adjacent to the air currents discharged through the openings 10a to 10c, it is possible to supply ions farther along the fast air currents discharged through the openings 10a to 10c.

Since the openings 10a to 10c are divided into upper and lower portions, and the speed of the air current discharged through the upper portion is higher than the speed of the air current discharged through the lower portion, the speeds of the air currents discharged through the outlet are gradually increased from the air current at the bottom to the air current at the top. Thus, it is possible to reduce the disturbance of the air currents and enhance the efficiency with which air is discharged.

Since the air current is discharged through the opening 10d such that the air current extends in the vertical direction due to the vertically increasing width portion 7, it is possible to vertically diffuse ions to the living space. Thus, it is possible to more sufficiently supply ions to the living space.

Moreover, since the air current is discharged through the opening 10d such that the air current extends in the lateral direction due to the laterally increasing width portion 8, it is possible to laterally diffuse ions to the living space. Thus, it is possible to more sufficiently supply ions to the living space.

Since the air currents are discharged through the opening 10a to 10c such that the air currents extend in the lateral direction due to the laterally increasing width portion 8, it is possible to reliably form the air curtain.

Since the air flow path 6 has the vertical division passages 11 to 14, which divide the outlet 10 vertically, and the speeds of the air currents flowing in the vertical division passages 11 to 13 at the upper portion are higher than the speed of the vertical division passage 14 at the lower portion, the air currents are discharged through the vertical division passages 11 to 13 at the upper portion to the space above the living space and thus the air currents function as the air curtain, with the result that it is possible to prevent the diffusion of the air current discharged through the vertical division passage 14 at the lower portion. In this way, it is possible to prevent ions from being diffused to the space above the living space and supply a sufficient amount of ions to the living space.

Since the fine particle generation device 17 is arranged in the vertical division passage 14 at the lower portion, ions are included in the slow air current discharged through the lower portion of the outlet 10, and thus it is possible to supply ions to the living space without the wind being sensed by a person.

Since the air flow path 6 extends upward from the blower fan 5 and bends frontward, and extends from the vicinity of the blower fan 5 to the outlet 10 to form the vertical division passages 11 to 14, the wetted perimeter of the cross section of the flow path is increased due to the vertical division passages 11 to 14, and thus the air currents easily flow along the wall surfaces of the vertical division passages 11 to 14. In this way, it is possible to increase the speed of air flowing in the upper portion of the air flow path 6, and reduce the separation and the disturbance of the air currents.

Since the air flow path 6 extends to the outlet 10 from the upstream side of the position intersecting the center of the curved surface portion 6a of the upper wall 6U of the air flow path 6 and the center of the curved surface portion 6b of the lower wall 6D, and thereby forms the vertical division passages 11 to 14, it is possible to reduce the air current separated from the lower wall 6D and the disturbance of the air currents.

Since the vertical division passage 14 at the lower portion is arranged on the inner circumferential side of the air outlet port 5c of the blower fan 5 with respect to the vertical division passages 11 to 13 at the upper portion, it is possible to increase the speeds of the air currents flowing in the vertical division passages 11 to 13 at the upper portion.

Since the vertical division passages 11 to 14 have the vertically increasing width portion 7, and the cross section of the vertically increasing width portion 7 perpendicular to the air current therein is formed in the shape of a laterally extending slit, the areas of portions of the upper and lower wall surfaces of the vertical division passages 11 to 14 in contact with the air currents flowing in the air flow path 6 are increased. Thus, it is possible to extend the air currents flowing in the vertical division passages 11 to 14 in the vertical direction without the air currents separating from the upper and lower wall surfaces. It is therefore possible to vertically diffuse ions to the living space.

Since the vertical division passages 11 to 14 have, on the downstream side of the vertically increasing width portion 7, the laterally increasing width portion 8 that increases its width as it extends from the upstream side to the downstream side and that extends the air currents in the lateral direction, it is possible not only to extend the air currents in the lateral direction and laterally diffuse ions to the living space but also to form the wide air curtain to prevent the upward diffusion of ions. It is also possible to easily form the air flow path 6 with high formability.

Since the laterally increasing width portion 8 has the lateral division passages 8a obtained by laterally dividing the vertical division passages 11 to 14, and the width of each of the lateral division passages 8a is increased laterally as it extends from the upstream side to the downstream side, the areas of portions of the left and right wall surfaces in contact with the air currents flowing in the air flow path 6 are increased. It is therefore possible to extend the air currents flowing in the lateral division passages 8a in the lateral direction without the air currents separating from the left and right wall surfaces.

Since the vertical division passage 14 in which the fine particle generation device 17 is arranged is provided with the narrowed portion 14a for narrowing the flow path on the upstream side of the fine particle generation device 17, the air current is narrowed and smoothed on the upstream side of the fine particle generation device 17. Since the speed of the air current is increased by the narrowed portion 14a, the concentration of ions near the fine particle generation device 17 is decreased. Thus, it is possible to generate a large number of ions with the fine particle generation device 17 and incorporate them into the air current. The narrowed portion 14a may be arranged at the position where the fine particle generation device 17 is arranged.

Since the lateral division passages 8a are provided in the laterally increasing width portion 8, which extends laterally in the air flow path 6, and either the positive ions or the negative ions are incorporated into each of the lateral division passages 8a, it is possible to reduce the collision of ions resulting from the air current curving and flowing in the air flow path 6. Hence, it is possible to reduce the destroying of ions, supply a sufficient number of ions into the living room and enhance the sterilization performance. When either the positive ions or the negative ions mainly flow in each of the lateral division passages 8a, even if a small number of the other ions are included, the effects described above can be obtained.

Since one of the electrodes 17a and 17b (first and second ion generation portions) is arranged near the open end of each of the lateral division passages 8a on the air inflow side, it is possible to easily pass either the positive ions or the negative ions through each of the lateral division passages 8a. The electrodes 17a and 17b (first and second ion generation portions) may be arranged within the lateral division passages 8a.

Since the positive ions flow in one of adjacent lateral division passages 8a, and the negative ions flow in the other of the adjacent lateral division passages 8a, it is possible to supply equal numbers of positive ions and negative ions to individual positions within the living room. Since equal numbers of positive ions and negative ions are necessary for killing airborne bacterial, it is possible to reliably obtain sterilization effects by supplying equal number of positive ions and negative ions.

Since the open ends of the lateral division passages 8a on the air inflow side are formed on the upstream side of the position intersecting the center of the curved surface portion 6c of the left wall 6L of the air flow path 6 and the center of the curved surface portion 6d of the right wall 6R, it is possible to reduce the air currents separating from the curved surface portions 6c and 6d. It is therefore possible to reduce the disturbance of the air currents and prevent the destroying of ions resulting from collision of the ions.

Since the vertical division passages 11 to 14, which vertically divide the air flow path 6, are provided, and the lateral division passages 8a are composed of thin passages obtained by laterally dividing the vertical division passages 11 to 14 on the side of the outlet 10, it is possible to smooth the air currents with the vertical division passages 11 to 14 and guide them to the lateral division passages 8a. It is also possible to prevent the generation of the backward current region H. It is therefore possible to further reduce the disturbance of the air currents and prevent the destroying of ions resulting from collision of the ions.

Since the ion generation device 17 is arranged in the vertical division passage 14 at the lower portion, and the speeds of the air currents flowing in the vertical division passages 11 to 13 at the upper portion are higher than the speed of the vertical division passage 14 at the lower portion, the air currents are discharged through the vertical division passages 11 to 13 at the upper portion to the space above the living space and thus the air currents function as the air curtain, with the result that it is possible to prevent the diffusion of the air current discharged through the vertical division passage 14 at the lower portion. In this way, it is possible to prevent ions from being diffused to the space above the living space and supply a sufficient number of ions to the living space. With a plurality of blower fans, air currents having different speeds may be formed.

A second embodiment will now be described. In the present embodiment, as shown in FIG. 7 described previously, the two vertical division passages 11 and 14 are provided vertically. Hence, two openings 10a and 10d (see FIG. 2) arranged vertically side by side are formed in the outlet 10 (see FIG. 2), and air currents are discharged through the openings 10a and 10d into the living room. The fine particle generation device 17 is provided in the vertical division passage 14. The other portions are the same as in the first embodiment.

FIGS. 22 and 23 are diagrams showing results obtained by examining the distribution of ions in the living room with the fine particle diffusion device 1 of the present embodiment. As in FIG. 11 described previously, the living room R is 4800 mm high, 6400 mm wide and 6400 mm deep. The fine particle diffusion device 1 is placed on the one side wall W1 and the floor surface F, and discharges an air current toward the side wall W2 opposite the side wall W1. The concentration of ions was measured on the vertical surface D passing through the center of the fine particle diffusion device 1 in the lateral direction.

FIG. 23 shows that, as compared with comparative examples 1 and 2 of FIGS. 15 and 17 described previously, it is possible to prevent the upward diffusion of ions and increase the concentration of ions in the living space in the lower portion of the living room R.

In the present embodiment, as in the first embodiment, the opening 10a (first outlet) through which the air current (first air current) is discharged upward is provided, and the opening 10d (second outlet) through which the air current (second air current) is discharged to a space below the above-mentioned air current is provided. Ions are included in the air current discharged through the opening 10d; ions are not included in the air current discharged through the opening 10a. Hence, the air current discharged through the opening 10a functions as the air curtain, and thus the ions included in the air current discharged through the opening 10d are not diffused to the space above the living space. In this way, it is possible to supply a sufficient number of ions to the living space. Part of ions having a lower concentration than the concentration of the ions discharged through the opening 10d may be discharged through the opening 10a.

A third embodiment will now be described. In the present embodiment, three division passages are provided vertically. Hence, as shown in FIG. 10 described previously, three openings 10a, 10b and 10d arranged vertically side by side are formed in the outlet 10 (see FIG. 2), and air currents are discharged through the openings 10a, 10b and 10d into the living room. The fine particle generation device 17 is provided in the division passage that has the opening 10d and is arranged at the lower portion. The other portions are the same as in the first embodiment.

As shown in FIG. 10, the speeds of air currents discharged through the openings 10a, 10b and 10d are stepwise varied from the air current at the top to the air current at the bottom. Thus, no eddy currents are generated, and the disturbance of the air currents are reduced. As shown in FIG. 24, the air currents including no ions are discharged through the openings 10a and 10b to the space above the living space, and the air current including ions are discharged through the opening 10d to the living space. Thus, it is possible to obtain the same effects as the first and second embodiments. Part of ions having a lower concentration than the concentration of the ions discharged through the opening 10d may be discharged through the openings 10a and 10b.

FIG. 25 is a side cross-sectional view schematically showing the fine particle diffusion device 1 of a fourth embodiment. For ease of description, the same portions as shown in FIGS. 1 and 2 described previously are identified with like symbols. The blower fan 5 of the present embodiment is formed with a sirocco fan or turbofan that sucks air in the direction of a shaft and that discharges the air in the circumferential direction. The other portions are the same as in the first and second embodiments.

The air flow path 6 extends upward from the blower fan 5 and bends frontward, and has the vertical division passages 11 and 14 divided vertically. The fine particle generation device 17 is arranged in the vertical division passage 14 at the lower portion. In the vertical division passage 14, the narrowed portion 14a is arranged at the position where the fine particle generation device 17 is arranged.

The blower fan 5 formed with a sirocco fan or turbofan is provided with a plurality of blades 5h on a disk 5g; air is sucked in the direction of the shaft and is discharged in the circumferential direction. Hence, the disk 5g is arranged opposite the air intake port 5a, and the vertical division passage 14 is arranged on the side of the air intake port 5a and the vertical division passage 11 is arranged on the side of the disk 5g. The speed of air discharged through the air outlet port 5c is slow on the side of the inlet 5b and is fast on the side of the disk 5g due to the viscosity of air. Hence, the vertical division passage 11 at the upper portion is provided on the side of the disk 5g, and thus it is possible to increase the speed of the air current discharged through the opening 10a. Therefore, the air intake port 5b is arranged on the side toward which the air flow path 6 is curved.

With the present embodiment, it is possible to obtain the same effects as in the first embodiment. Part of ions having a lower concentration than the concentration of the ions discharged through the opening 10d may be discharged through the opening 10a.

A fifth embodiment will now be described. In the present embodiment, each of the electrodes 17a and 17b shown in FIG. 8 described previously can switch ions between positive ions and negative ions and generate them. The other portions are the same as in the first embodiment shown in FIGS. 1 to 8.

The polarities of ions generated by the electrodes 17a and 17b are switched every predetermined period. Specifically, as shown in FIG. 8 described previously, positive ions are generated from the electrode 17a, and negative ions are generated from the electrode 17b as in the first embodiment. When the predetermined period elapses, as shown in FIG. 26, negative ions are generated from the electrode 17a, and positive ions are generated from the electrode 17b. Then, when the predetermined period elapses, ions are generated as shown in FIG. 8.

In this way, positive ions and negative ions are alternately discharged into the left and right edges of the air currents that extend laterally in the laterally increasing width portion 8 and that are discharged. It is therefore possible to distribute positive ions and negative ions of high concentration laterally and widely to the living room.

FIG. 27 is a diagram showing results obtained by examining the distribution of ions in the living room with the fine particle diffusion device 1 of the present embodiment. As in FIG. 11 described previously, the living room R is 4800 mm high, 6400 mm wide and 6400 mm deep. The fine particle diffusion device 1 is placed on the one side wall W1 and the floor surface F, and discharges an air current toward the side wall W2 opposite the side wall W1. The concentration of ions indicates the concentration of which of the positive ions and the negative ions are fewer in number on the horizontal surface E at a height of 1600 mm. The figure shows that the concentration of ions can be increased over a further wide area in the lateral direction as compared with the first embodiment.

In the present embodiment, since the polarities of ions generated by the electrodes 17a and 17b (first and second ion generation portions) are switched every predetermined period, it is possible to distribute positive ions and negative ions of high concentration laterally and widely to the living room. Thus, it is possible to further enhance the sterilization performance. Moreover, since the polarities of ions flowing in the air flow path 6 are alternately switched, it is possible to reduce charging of the air flow path 6 and thus prevent the adherence of dust and the like.

A sixth embodiment will now be described. In the present embodiment, as shown in FIG. 28, the electrodes 17a and 17b are arranged near the open end of each of the lateral division passages 8a on the air inflow side. The other portions are the same as in the first embodiment. The electrodes 17a and 17b for each of the lateral division passages 8a are alternately driven. In the figure, the electrodes 17a and 17b in the upper row are driven, and thereafter the electrodes 17a and 17b in the lower row are driven. Consequently, when the electrode 17a is driven in one of the lateral division passages 8a to generate positive ions, the electrode 17b is driven in the lateral division passage 8a adjacent to the one of the lateral division passages 8a to generate negative ions.

In this way, as in the fifth embodiment, positive ions and negative ions are alternately discharged into the left and right edges of the air currents that extend laterally in the laterally increasing width portion 8 and that are discharged. It is therefore possible to distribute positive ions and negative ions of high concentration laterally and widely to the living room. Moreover, since the polarities of ions flowing in the air flow path 6 are alternately switched, it is possible to reduce charging of the air flow path 6 and thus prevent the adherence of dust and the like.

In the first to sixth embodiments, the fine particle diffusion device 1 sterilizes the living room by generating positive ions and negative ions with the fine particle generation device 17 and then discharging them through the outlet 10. As the fine particle diffusion device 1, a fine particle diffusion device 1 may be used that obtains relaxation effects by generating only negative ions with the fine particle generation device 17. As the fine particle diffusion device 1, a fine particle diffusion device 1 may also be used that, for example, removes smells, kill insects or kill bacteria within a living room by generating, an aromatic substance, a deodorant, an insecticide, a bactericide or the like with the fine particle generation device 17.

INDUSTRIAL APPLICABILITY

The present invention can be applied to a fine particle diffusion device that discharges and diffuses into a room fine particles of ions, an aromatic substance, a deodorant, an insecticide, a bactericide or the like.

LIST OF REFERENCE SYMBOLS

1 Fine particle diffusion device
2 Main body enclosure
3 Inlet
4 Air filter
5 Blower fan
6 Air flow path
6a and 6b Curved surface portion
7 Vertically increasing width portion
8 Laterally increasing width portion
8a Lateral division passage
10 Outlet
10a to 10d Opening
11 to 14 Vertical division passage
17 Fine particle generation device
17a, 17b and 17c Electrode

The invention claimed is:

1. A fine particle diffusion device comprising:
an ion generation device including a first ion generation portion that generates only a positive ion and a second ion generation portion that generates only a negative ion;
a blower fan; and
an air flow path that guides, by driving of the blower fan, the ions generated by the ion generation device to an outlet,
wherein the air flow path includes a plurality of lateral division passages whose lateral widths are increased as the lateral division passages extend from an upstream side to a downstream side and which are divided laterally, and
the ion generated by the first ion generation portion flows only in a first of the lateral division passages, and the ion generated by the second ion generation portion flows only in a second of the lateral division passages.

2. The fine particle diffusion device of claim 1,
wherein the first ion generation portion is arranged either in the first of the lateral division passages or in a vicinity of an open end of the first of the lateral division passages on an air inflow side, and
the second ion generation portion is arranged either in the second of the lateral division passages or in a vicinity of an open end of the second of the lateral division passages on an air inflow side.

3. The fine particle diffusion device of claim 1,
wherein the first ion generation portion and the second ion generation portion are alternately arranged according to each of the lateral division passages, and
the first of the lateral division passages and the second of the lateral division passages are adjacent to each other.

4. The fine particle diffusion device of claim 1,
wherein the air flow path is provided with a left wall having a curved surface portion and a right wall having a curved surface portion and extends toward both sides, and open ends of the lateral division passages on an air inflow side are formed on an upstream side of a position intersecting a center of the curved surface portion of the left wall and a center of the curved surface portion of the right wall.

5. The fine particle diffusion device of claim 1, further comprising:
vertical division passages that divide the air flow path vertically,
wherein the lateral division passages are composed of thin passages that laterally divide the vertical division passages on a side of the outlet.

6. The fine particle diffusion device of claim 5,
wherein the ion generation device is arranged in one of the vertical division passages at a lower portion, and a speed of an air current flowing in one of the vertical division passages at an upper portion is higher than a speed of an air current flowing in the vertical division passage at the lower portion.

7. The fine particle diffusion device comprising:
an ion generation device including a first ion generation portion that generates only a positive ion and a second ion generation portion that generates only a negative ion;
a blower fan; and
an air flow path that guides, by driving of the blower fan, the ions generated by the ion generation device to an outlet,
wherein the air flow path includes a plurality of lateral division passages whose lateral widths are increased as the lateral division passages extend from an upstream side to a downstream side and which are divided laterally,
the first ion generation portion and the second ion generation portion are arranged either in the first of the lateral division passages or in a vicinity of an open end of the first of the lateral division passages on an air inflow side,
the first ion generation portion and the second ion generation portion are either in the second of the lateral division passages or in a vicinity of an open end of the second of the lateral division passages on an air inflow side and
a first period during which the ion generated by the first ion generation portion flows only in the first of the lateral division passages and the ion generated by the second ion generation portion flows only in the second of the lateral division passages and a second period during which the ion generated by the second ion generation portion flows only in the first of the lateral division passages and the ion generated by the first ion generation portion flows only in the second of the lateral division passages are provided.

* * * * *